United States Patent

Alder et al.

Patent Number: 4,677,129
Date of Patent: Jun. 30, 1987

[54] SUBSTITUTED-3-AZABICYCLO[3.1.1]HEPTANE-2,4-DIONES USEFUL FOR TREATING HORMONE-DEPENDENT DISEASES

[75] Inventors: Alex Alder, Basel; Jaroslav Stanek, Birsfelden; Daniel Bellus, Riehen, all of Switzerland

[73] Assignee: Ciba-Geigy Corporation, Ardsley, N.Y.

[21] Appl. No.: 746,814

[22] Filed: Jun. 20, 1985

[30] Foreign Application Priority Data

Jun. 20, 1984 [CH] Switzerland .................. 2987/84

[51] Int. Cl.⁴ .................. A61K 31/435; C07D 221/22
[52] U.S. Cl. .................. 514/299; 546/183; 560/123; 560/147; 562/505
[58] Field of Search .................. 546/183; 514/299

[56] References Cited

U.S. PATENT DOCUMENTS 2,673,205 3/1954 Hoffmann et al. .................. 546/219

FOREIGN PATENT DOCUMENTS 166692 1/1986 European Pat. Off. ............ 546/183

*Primary Examiner*—Donald G. Daus
*Assistant Examiner*—Cecilia Shen

*Attorney, Agent, or Firm*—Michael W. Glynn; Irving M. Fishman

[57] ABSTRACT

1-phenyl-3-azabicyclo[3.1.1]-heptane-2,4-diones of the formula

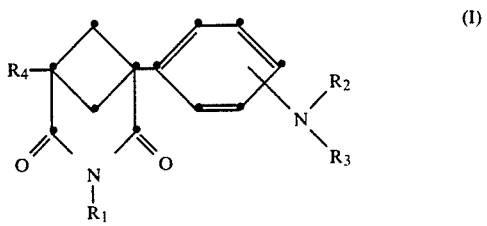

in which $R_1$ represents hydrogen or a saturated or unsaturated, aliphatic, cycloaliphatic, cycloaliphatic-aliphatic, aromatic or aromatic-aliphatic hydrocarbon radical having up to and including 18, preferably up to and including 12, carbon atoms, $R_2$ represents hydrogen, lower alkyl, sulpho or acyl, $R_3$ represents hydrogen or lower alkyl and $R_4$ represents hydrogen, lower alkyl, phenyl or phenyl substituted by $-N(R_2)(R_3)$, and salts of these compounds, have valuable pharmacological properties, are effective as aromatase inhibitors and can therefore be used for the treatment of hormone-dependent diseases, especially mammary carcinoma.

25 Claims, No Drawings

SUBSTITUTED-3-AZABICYCLO[3.1.1]HEPTANE-2,4-DIONES USEFUL FOR TREATING HORMONE-DEPENDENT DISEASES

The present invention relates to novel aminophenyl-substituted azabicycloalkanes having valuable pharmacological properties and to salts of these compounds, to the use of these substances and pharmaceutical preparations that contain these substances, to pharmaceutical preparations and to processes for the manufacture of these novel substances, and also to intermediates and processes for the manufacture of these intermediates.

The present invention relates to substituted 1-phenyl-3-azabicyclo[3.1.1]heptane-2,4-diones of the formula

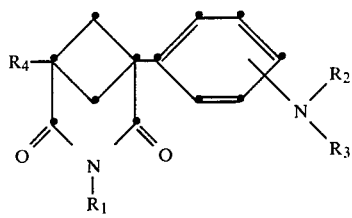

in which $R_1$ represents hydrogen or a saturated or unsaturated, aliphatic, cycloaliphatic, cycloaliphatic-aliphatic, aromatic or aromatic-aliphatic hydrocarbon radical having up to and including 18, preferably up to and including 12, carbon atoms, $R_2$ represents hydrogen, lower alkyl, sulpho or acyl, $R_3$ represents hydrogen or lower alkyl and $R_4$ represents hydrogen, lower alkyl, phenyl or phenyl substituted by —$N(R_2)(R_3)$, and to salts of these compounds.

In the description of the present invention, the term "lower" used in the definition of groups or radicals, for example lower alkyl, lower alkoxy, lower alkanoyl, etc., denotes that the groups or radicals so defined, unless expressly defined otherwise, contain up to and including 7, and preferably up to and including 4, carbon atoms.

The general terms and definitions used in the description preferably have the following meanings:

The group —$N(R_2)(R_3)$ may be in the 2-, 3- or 4-position of the phenyl radical.

A saturated or unsaturated, aliphatic, cycloaliphatic or cycloaliphatic-aliphatic hydrocarbon radical $R_1$ is, for example, alkyl, alkenyl, lower alkynyl, cycloalkyl, cycloalkenyl, cycloalkyl-lower alkyl, cycloalkyl-lower alkenyl, cycloalkenyl-lower alkyl or unsubstituted or substituted aryl or aryl-lower alkyl.

Alkyl $R_1$ has, for example, from 1 to 12 carbon atoms and is, for example, lower alkyl having from 1 to 7 carbon atoms, for example methyl, ethyl, n-propyl, isopropyl, n-butyl, isobutyl, tert.-butyl, n-pentyl, neopentyl, n-hexyl or n-heptyl, and n-octyl, n-nonyl, n-decyl, n-undecyl or n-dodecyl.

Alkenyl $R_1$ has, for example, from 2 to 12 carbon atoms and is, for example, lower alkenyl having from 3 to 7 carbon atoms, for example allyl or 2- or 3-butenyl, and 2-octenyl, 2-nonenyl, 2-decenyl, 2-undecenyl or 2-dodecenyl, it also being possible for the double bond to be in a position other than the 2-position.

Lower alkynyl $R_1$ has, for example, from 2 to 7, especially from 3 to 4, carbon atoms and is, for example, 2-propynyl or 2-butynyl.

Cycloalkyl $R_1$ contains, for example, from 3 to 10, especially from 3 to 6, carbon atoms and is, for example, cyclopropyl, cyclobutyl, cyclopentyl or cyclohexyl.

Cycloalkenyl $R_1$ contains, for example, from 3 to 10, especially from 3 to 6, carbon atoms and is, for example, 2-cyclohexenyl or 2,5-cyclohexadienyl.

Cycloalkyl-lower alkyl $R_1$ contains, for example, from 4 to 10, especially from 4 to 7, carbon atoms and is, for example, cyclopropylmethyl, cyclobutylmethyl, cyclopentylmethyl or cyclohexylmethyl, and 2-cyclopropylethyl, 2-cyclobutylethyl, 2-cyclopentylethyl or 2-cyclohexylethyl.

Cycloalkyl-lower alkenyl $R_1$ contains, for example, from 5 to 10, especially from 4 to 9, carbon atoms and is, for example, cyclohexylvinyl or cyclohexylallyl.

Cycloalkenyl-lower alkyl $R_1$ contains, for example, from 4 to 10, especially from 4 to 8, carbon atoms and is for example, 1-cyclohexenylmethyl or 1,4-cyclohexadienylmethyl, and 2-(1-cyclohexenyl)-ethyl or 2-(1,4-cyclohexadienyl)-ethyl.

Unsubstituted or substituted aryl $R_1$ has, for example, from 6 to 12 carbon atoms and is, for example, phenyl or 1- or 2-naphthyl, the phenyl or naphthyl being optionally substituted by lower alkyl, hydroxy, lower alkoxy, acyloxy, amino, lower alkylamino, di-lower alkylamino, acylamino or by halo, the substituents, of which there may be several, being in the 2-, 3- or 4- position of the phenyl ring, for example 4-methylphenyl, 4-methyl-1-naphthyl, 4-hydroxyphenyl, 3- or 4-methoxyphenyl, 3,4-dimethoxyphenyl, 4-acetoxyphenyl, 3-or 4-dimethylaminophenyl, 4-acetaminophenyl, 3- or 4-chlorophenyl or 4-bromophenyl.

Unsubstituted or substituted aryl-lower alkyl $R_1$ has, for example, from 7 to 15 carbon atoms and is, for example, benzyl, 2-phenylethyl or 1- or 2-naphthylmethyl, it being possible for the aryl radical to be substituted by the same groups as in aryl $R_1$, for example 4-methylbenzyl, 4-methoxybenzyl, 3,4-dimethoxybenzyl, 2-(4-methoxyphenyl)-ethyl or 4-dimethylaminobenzyl.

Lower alkyl $R_2$ or $R_3$ has the meanings given under $R_1$ and is preferably methyl or ethyl.

Acyl $R_2$ has, for example, up to 19 carbon atoms and is derived from a carboxylic acid, a semiester of carbonic acid, carbamic acid, a substituted carbamic acid, a sulphonic acid, amidosulphonic acid or a substituted amidosulphonic acid.

Acyl $R_2$ has, for example, the formula: $R^b$—CO—, $R^a$—O—CO—, $(R^b)(R^b)N$—CO—, $R^a$—$SO_2$— or $(R^b)(R^b)N$—$SO_2$— in which $R^a$ represents a saturated or unsaturated, aliphatic, cycloaliphatic or cycloaliphatic-aliphatic hydrocarbon radical having up to and including 18, preferably up to and including 10, carbon atoms or an aromatic or aromatic-aliphatic hydrocarbon radical having up to and including 18, preferably up to and including 10, carbon atoms, and $R^b$ represents hydrogen or has the meanings of $R^a$, it being possible if two radicals $R^b$ are present for the two radicals $R^b$ to be the same or different.

A saturated or unsaturated, aliphatic, cycloaliphatic or cycloaliphatic-aliphatic hydrocarbon radical $R^a$ or $R^b$ has the meanings given under $R_1$ and is preferably lower alkyl, for example methyl or ethyl.

An aromatic or aromatic-aliphatic hydrocarbon radical $R^a$ or $R^b$ is, for example, phenyl, phenyl-lower alkyl, for example benzyl, or diphenylmethyl.

Acyl $R_2$ is preferably lower alkanoyl, for example formyl or acetyl, or lower alkanesulphonyl, for example methane- or ethane-sulphonyl.

Lower alkyl $R_4$ is, for example, methyl, ethyl, n-propyl, isopropyl, n-butyl, isobutyl, tert.-butyl, n-pentyl, neopentyl, n-hexyl or n-heptyl.

In a phenyl radical $R_4$ substituted by $-N(R_2)(R_3)$, $R_2$ and $R_3$ have the meanings given above, it being possible for the phenyl ring to be substituted in the 2-, 3- or 4-position.

Salts of compounds of the formula I according to the invention having a salt-forming group are especially pharmaceutically acceptable non-toxic salts.

Such salts are formed, for example, by the amino group at the phenyl ring by the addition of an inorganic acid, for example hydrochloric acid, sulphuric acid, lower alkanesulphonic acid or phosphoric acid, and are, for example, hydrochlorides, bisulphates, methanesulphonates, hydrogen phosphates or dihydrogen phosphates.

Other acid addition salts are formed, for example, from carboxylic acids and are, for example, formates, acetates, trifluoroacetates, benzoates, citrates, tartrates or salicylates.

The compounds of the formula I may also be in the form of hydrates.

The present invention relates especially to compounds of the formula I in which $R_1$ represents hydrogen, alkyl, alkenyl, lower alkynyl, cycloalkyl, cycloalkenyl, cycloalkyl-lower alkyl, cycloalkyl-lower alkenyl, cycloalkenyl-lower alkyl or unsubstituted or substituted aryl or aryl-lower alkyl, $R_2$ represents hydrogen, lower alkyl, sulpho, lower alkanoyl or lower alkanesulphonyl, $R_3$ represents hydrogen or lower alkyl and $R_4$ represents hydrogen, lower alkyl, phenyl or phenyl substituted by $-N(R_2)(R_3)$, and to salts thereof, especially pharmaceutically acceptable salts thereof.

The present invention relates more especially to compounds of the formula I in which $R_1$ represents hydrogen, alkyl having up to and including 12 carbon atoms, for example lower alkyl, for example methyl, ethyl, n-propyl, isopropyl, n-butyl, isobutyl, tert.-butyl, n-pentyl, neopentyl, n-hexyl or n-heptyl, and n-octyl, n-nonyl, n-decyl, n-undecyl or n-dodecyl, lower alkenyl, for example allyl or 2-butenyl, lower alkynyl, for example 2-propynyl or 2-butynyl, cycloalkyl, for example cyclopropyl, cyclopentyl or cyclohexyl, cycloalkyl-lower alkyl, for example cyclopentylmethyl or cyclohexylmethyl, or unsubstituted or substituted aryl-lower alkyl, for example benzyl or 4-methoxybenzyl, $R_2$ represents hydrogen, lower alkyl, for example methyl, lower alkanoyl, for example acetyl, or lower alkanesulphonyl, for example methanesulphonyl, $R_3$ represents hydrogen or lower alkyl, for example methyl, and $R_4$ represents hydrogen, lower alkyl, for example methyl, ethyl, n-propyl, isopropyl, n-butyl, isobutyl or tert.-butyl, phenyl or phenyl substituted by $-N(R_2)(R_3)$, and to salts thereof, especially pharmaceutically acceptable salts thereof.

The present invention relates especially to compounds of the formula I in which $R_1$ represents hydrogen, lower alkyl, for example methyl, ethyl, n-propyl, isopropyl, n-butyl, isobutyl, tert.-butyl, n-pentyl, neopentyl, n-hexyl or n-heptyl, lower alkenyl, for example allyl, lower alkynyl, for example 2-propynyl, cycloalkyl, for example cyclohexyl, cycloalkyl-lower alkyl, for example cyclohexylmethyl, $R_2$ and $R_3$ represent hydrogen and $R_4$ represents hydrogen, lower alkyl, for example methyl, ethyl, n-propyl, isopropyl, n-butyl, isobutyl or tert.-butyl, phenyl or phenyl substituted by $-N(R_2)(R_3)$, and to pharmaceutically acceptable salts thereof.

The present invention relates more especially to compounds of the formula I in which the group $-N(R_2)(R_3)$ is in the 4-position of the phenyl radical, $R_1$ represents hydrogen, lower alkyl, for example methyl, ethyl, n-propyl, isopropyl, n-butyl, isobutyl or tert.-butyl, lower alkenyl, for example allyl, lower alkynyl, for example 2-propynyl, cycloalkyl-lower alkyl, for example cyclohexylmethyl, $R_2$ and $R_3$ represent hydrogen and $R_4$ represents hydrogen or lower alkyl, for example methyl, ethyl, n-propyl, isopropyl, n-butyl, isobutyl or tert.-butyl, and to pharmaceutically acceptable salts thereof.

The invention relates very especially to compounds of the formula I in which the group $-N(R_2)(R_3)$ is in the 4-position of the phenyl radical, $R_1$ represents hydrogen, alkyl having up to and including 12 carbon atoms, for example lower alkyl, such as methyl, ethyl, n-propyl, isopropyl, n-butyl, isobutyl, n-pentyl, neopentyl, n-hexyl or n-heptyl, and n-octyl, n-nonyl, n-decyl, n-undecyl or n-dodecyl, lower alkenyl, for example allyl, lower alkynyl, for example 2-propynyl, cycloalkyl, for example cyclopentyl or cyclohexyl, cycloalkyl-methyl, for example cyclopentylmethyl or cyclohexylmethyl, benzyl or benzyl substituted by lower alkyl, hydroxy, lower alkoxy or by lower alkanoyloxy, for example 4-methoxybenzyl, and $R_2$, $R_3$ and $R_4$ represent hydrogen, and to pharmaceutically acceptable salts thereof.

The present invention relates especially to the compounds mentioned in the Examples.

The invention also relates to pharmaceutical preparations containing compounds of the formula I in which $R_1$, $R_2$, $R_3$ and $R_4$ have the above meanings, and to the use of these compounds in a method for the treatment of the human or animal body.

The novel compounds of the formula I and their pharmaceutically acceptable salts have valuable pharmacological properties, for example, as aromatase inhibitors. The suitability of compounds of the formula I as aromatase inhibitors can be demonstrated in vitro using human placental microsomes in the "aromatase assay" according to P. E. Graves and H. A. Salhanick, Endocrinology, Vol. 105, p. 52 (1979). In this test procedure, the formation of water having tritium isotopes and $17\beta$-oestradiol from $[1\beta,2\beta$-$^3$H]-testosterone as a result of the action of a compound of the formula I on the formation of the hydrogenated form of the aromatase coenzyme, nicotinamide adenine dinucleotide phosphate (NADPH), is measured. The addition of a compound of the formula I according to the invention, for example of 1-(4-aminophenyl)-3-n-propyl-3-azabicyclo[3.1.1]heptane-2,4-dione, substantially reduces the enzyme activity (NADPH content), resulting in a markedly lower content of water having radioactive tritium isotopes than in the case of measurements made without the addition of a compound of the formula I according to the invention. Furthermore, comparison measurements show that, at the same concentrations, the reduction in enzyme activity resulting from the addition of a compound of the formula I according to the invention, for example of 1-(4-aminophenyl)-3-n-propyl-3-azabicyclo[3.1.1]-heptane-2,4-dione, is substantially greater than that resulting from the addition of other known aromatase inhibitors, for example aminoglutethimide.

On account of their activity as aromatase inhibitors, the compounds of the formula I in which $R_1$, $R_2$, $R_3$ and R₄ have the meanings given above, or salts thereof, can be used as medicaments, for example in the form of pharmaceutical preparations, for the treatment of hormone-dependent disorders, for example hormone-dependent tumours, such as tumours dependent on the overproduction of oestrogen, especially mammary carcinoma, and hormonal anomalies, for example gynaecomastia or prostate hyperplasia, in warm-blooded animals (humans and animals) by enteral, for example oral, or parenteral administration of therapeutically effective doses.

The present invention also relates to the use of these compounds as medicaments, especially those having a carcinostatic action, in one of the mentioned methods for the treatment of the human or animal body.

The daily doses of such compounds for mammals, depending on the species, and for humans, depending on age and individual condition and on the method of administration, are from approximately 1 mg to approximately 100 mg, especially from 5 mg to approximately 50 mg, per kg body weight. Within this range, the doses are generally lower for parenteral administration, for example intramuscular or subcutaneous injection or intravenous infusion, than for enteral, that is to say oral or rectal, administration.

The compounds of the formula I and pharmaceutically acceptable salts of such compounds having salt-forming properties are administered orally or rectally preferably in dosage unit forms, such as tablets, dragées or capsules or suppositories, and parenterally especially in the form of injectable solutions, emulsions or suspensions or in the form of infusion solutions, there coming into consideration as solutions especially solutions of salts.

The invention also relates to pharmaceutical preparations for enteral, for example oral or rectal, administration or for parenteral administration that contain a therapeutically effective amount of a compound of the formula I, or of a pharmaceutically acceptable salt of such a compound having a salt-forming group, optionally together with a pharmaceutically acceptable carrier or mixture of carriers, there being used as carriers solid or liquid, inorganic or organic substances. Appropriate dosage unit forms, especially for peroral administration, for example dragées, tablets or capsules, preferably contain from approximately 50 mg to approximately 500 mg, especially from approximately 100 mg to approximately 400 mg, of a compound of the formula I, or of a pharmaceutically acceptable salt of such a compound that is capable of salt formation, together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium biphosphate, and also binders, such as starch pastes using, for example, corn, wheat, rice or potato starch, gelatine, tragacanth, methylcellulose and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores can be provided with suitable coatings which are optionally resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose-preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules can contain the active ingredient in the form of a granulate, for example in admixture with fillers, such as lactose, binders, such as starches, and/or glidants, such as talc or magnesium stearate, and optionally stabilisers. In soft capsules the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories that consist of a combination of the active ingredient with a suppository base. Suitable suppository bases are, for example, natural or synthetic triglycerides, paraffin hydrocarbons, polyethylene glycols or higher alkanols. It is also possible to use gelatine rectal capsules that contain a combination of the active ingredient with a base material; as base materials there come into consideration, for example, liquid triglycerides, polyethylene glycols or paraffin hydrocarbons.

Especially suitable for parenteral administration are aqueous solutions of an active ingredient in water-soluble form, for example a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain substances that increase the viscosity, for example sodium carboxymethylcellulose, sorbitol and/or dextran, and, optionally, stabilisers.

The pharmaceutical preparations of the present invention can be manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores.

The present invention also relates to processes for the manufacture of compounds of the formula I and salts thereof. These can be manufactured according to methods known per se, for example as follows:

(a) in a compound of the formula

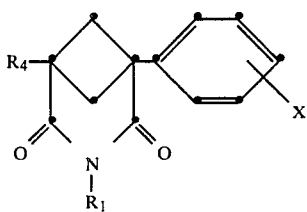

(II)

in which $R_1$ and $R_4$ have the meanings given under formula I and X is a group that can be converted into the group $-N(R_2)(R_3)$, or in a salt thereof, X is converted into the group $-N(R_2)(R_3)$, or (b) a compound of the formula

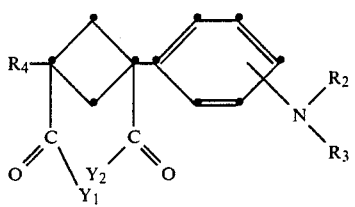

(III)

in which $R_2$, $R_3$ and $R_4$ have the meanings given under formula I and $Y_1$ and $Y_2$ represent leaving groups, or a salt thereof, is cyclised by reaction with a compound that yields the group $<N-R_1$, or (c) a compound of the formula

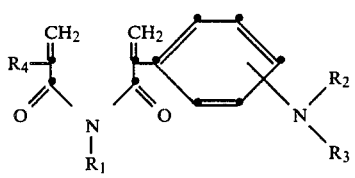

(IV)

in which $R_1$, $R_2$, $R_3$ and $R_4$ have the meanings given under formula I, or a salt thereof, is cyclised, or (d) a compound of the formula

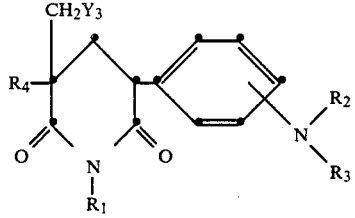

(V)

or

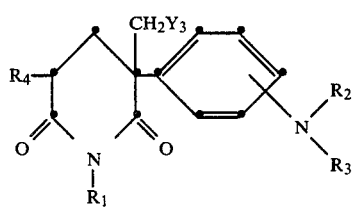

(VI)

in which $R_1$, $R_2$, $R_3$ and $R_4$ have the meanings given under formula I and $Y_3$ represents a leaving group, or a salt thereof, is cyclised with a base, and, if desired, a compound of the formula I obtainable according to the invention is converted into a different compound of the formula I according to the definition and/or a resulting salt is converted into the free compound or into a different salt and/or a resulting free compound is converted into a salt and/or a resulting mixture of isomers is separated into the individual isomers.

Process (a)

In a compound of the formula II, a group X that can be converted into the group $-N(R_2)(R_3)$ is, for example, a nitrogen-containing reducible group, for example a nitro, nitroso, hydroxyamino or azido group, a replaceable group, for example halogen, for example chlorine, bromine or iodine, or a derivatised carboxy group, for example a carbamoyl or azidocarbonyl group, or a protected amino group from which the protecting group is removed and replaced by hydrogen.

A nitrogen-containing reducible group, for example a nitro, nitroso, hydroxyamino or azido group, is converted into the amino group by a customary reducing agent which, if desired, is used in the presence of a suitable catalyst and/or carrier.

As a customary reducing agent there comes into consideration especially: catalytically activated hydrogen, there being used as hydrogenation catalyst, for example, a noble metal catalyst, for example a palladium, platinum, rhodium or nickel catalyst, or a noble metal compound, for example platinum dioxide, which, if desired, is used with a suitable carrier, such as carbon, barium sulphate or carbonate or calcium carbonate; a reducing tin(II) or iron(II) salt, which is used, for example, in the form of a chloride and, in the latter case, also in the form of a sulphate; a reducing dithionite or sulphite salt, for example sodium dithionite, sodium sulphite or sodium bisulphite; an optionally activated base metal, for example activated iron, tin, zinc or aluminium, which is activated optionally in the presence of the corresponding metal salt or a neutral salt, for example calcium, magnesium, potassium or sodium chloride; and also a sulphide, for example hydrogen sulphide; a di-or poly-sulphide, for example sodium disulphide or sodium polysulphide; an alkali metal sulphide or alkali metal bisulphide, for example sodium sulphide or sodium bisulphide; ammonium sulphide or ammonium polysulphide; a reducing agent that yields hydrogen, for example unsubstituted or substituted hydrazine, for example hydrazine or phenylhydrazine, which is added optionally in the form of an acid addition salt, for example in the form of a hydrochloride; or molecular hydrogen which is generated by electrolytic reduction of protons at the cathode.

The reduction with catalytically activated hydrogen is carried out at normal pressure or elevated pressure, for example up to approximately 5 bar. The reduction with the mentioned reducing agents is carried out in an acidic medium, for example in an acetic acid medium, or in a neutral medium. The reduction with iron(II) salts is carried out under basic conditions and the reducing iron(II) hydroxide precipitates. The reductions with dithionite salts and sulphides also take place under basic conditions.

The reduction with agents that yield hydrogen, for example hydrazines, is accelerated by the above-mentioned hydrogenation catalysts, for example Raney nickel, palladium-on-carbon or platinum. The electrolytic reduction of the nitro groups to form the amine is carried out at cathodes consisting of metals having high overpotential, such as lead, tin, nickel, copper or zinc. The electrolysis is generally carried out in a solution of sulphuric acid or hydrochloric acid.

The above-mentioned reducing agents are added in at least an equimolar amount, preferably in excess. The addition of an excess of reducing agent is to prevent the formation of intermediates, for example nitroso or hydroxyamino compounds.

The reduction is preferably carried out in a solvent, for example a lower alkanol, for example methanol or ethanol, a lower alkoxy-lower alkanol, for example 2-methoxy- or 2-ethoxy-ethanol, a lower alkanecarboxylic acid or an ester thereof, for example acetic acid and ethyl acetate, and also an ether, for example diethyl ether, tetrahydrofuran or dioxan.

To increase the solubility especially of the salt-type reducing agents in the reaction mixture, water can be added to the reaction mixture as required. The reaction is customarily carried out at temperatures of from approximately $-20°$ to approximately $100°$ C., although it can also be carried out at lower temperatures if highly reactive activators are used.

In a compound of the formula II, a replaceable group X, for example halogen, for example chlorine, bromine or iodine, is converted into the group $-N(R_2)(R_3)$ using a compound that yields the group $-N(R_2)(R_3)$, for example a compound of the formula $H-N(R_2)(R_3)$ or a metal compound thereof, such as ammonia, an alkali metal amide, for example lithium, sodium or potassium amide, a lower alkylamine, for example methylamine, a di-lower alkylamine, for example dimethylamine, or an acid amide in which a hydrogen atom of the amide group has been replaced by an alkali metal, for example lithium, for example $R^a-CO-NR_3Li$.

The reaction of a compound of the formula II in which X represents halogen, for example chlorine, with a compound that yields the group $-N(R_2)(R_3)$, for example with ammonia, preferably takes place in the presence of a catalyst, for example copper(I) oxide or copper(II) oxide, copper(I) chloride or copper(II) chloride or copper sulphate. The reaction is carried out in a concentrated aqueous ammonia solution or, preferably, in liquid ammonia, and the reaction conditions given in Houben-Weyl, Methoden der Organischen Chemie (hereinafter referred to as "Houben-Weyl"), Vol. XI/1 "Stickstoffverbindungen", pp. 63–67, are observed, for example elevated temperature above 100° and elevated pressure.

The reaction of a compound of the formula II in which X represents halogen, for example chlorine, is preferably carried out with an alkali metal amide, for example lithium or potassium amide. The amide is advantageously added in the form of a suspension.

As solvent there is preferably used benzene or toluene and the operation is carried out in an inert gas atmosphere, for example a nitrogen atmosphere. The reaction is best carried out at elevated temperature, for example at the boiling temperature of the reaction mixture, analogously to the reaction conditions described for aromatic halogen compounds in Houben-Weyl, Vol. XI/1 "Stickstoffverbindungen", on pp. 74–79.

In a compound of the formula II, a derivatised carboxy group X, for example carbamoyl or azidocarbonyl, can be converted into the amino group under the reaction conditions known for reactions or degradation reactions according to Hofmann (carbamoyl) or Curtius (azidocarbonyl).

The conversion according to Hofmann of the carbamoyl compound (carboxylic acid amide) of the formula II into the amino compound of the formula I using free halogen, for example bromine, is carried out under alkaline conditions.

The conversion according to Curtius of the azidocarbonyl compound of the formula II into the amino compound of the formula I is carried out thermally with decomposition of the azidocarbonyl group.

After the rearrangement, hydrolysis is carried out under acidic conditions, for example in a dilute, aqueous mineral acid, for example in dilute sulphuric acid.

The reaction conditions for the Hofmann and Curtius degradation are described in the survey by P. A. Smith, Org. Reactions 3, 363 (1946).

Protected amino groups from which the protecting group can be removed and replaced by hydrogen are described, for example, in McOmie, "Protective Groups in Organic Chemistry", Plenum Press, London and New York, 1973, in "The Peptides", Vol. I, Schröder and Lubke, Academic Press, London and New York, 1965, and in Houben-Weyl, Vol. 15/1, Georg Thieme Verlag, Stuttgart, 1974.

Preferred protecting groups are groups that can be removed by acidolysis, for example lower alkoxycarbonyl, for example tert.-butoxycarbonyl (BOC) or 2-halo-lower alkoxycarbonyl, for example 2-iodoethoxycarbonyl or 2,2,2-trichloroethoxycarbonyl.

It is also possible, however, to use amino-protecting groups that can be removed by reduction or under mild conditions with a base, for example especially a benzyloxycarbonyl group or a benzyloxycarbonyl group in which the phenyl radical is substituted by halogen atoms, nitro groups and/or by lower alkoxy groups, for example the p-chloro-, p-nitro- or p-methoxy-benzyloxycarbonyl group.

The removal of the protecting group is carried out in the manner generally known; the acid hydrolysis (acidolysis) is carried out, for example, by means of trifluoroacetic acid. The groups that can be removed by reduction, especially those which contain benzyl radicals, are preferably removed by hydrogenolysis, for example by hydrogenation with palladium catalysis.

Process (b)

In a compound of the formula III, each of the leaving groups $Y_1$ and $Y_2$, independently of the other, is, for example, hydroxy, halogen, for example chlorine, bromine or iodine, lower alkoxy, silyloxy or sulphonyloxy.

Lower alkoxy $Y_1$ or $Y_2$ is, for example, methoxy, ethoxy, n-propoxy, branched lower alkoxy, for example tert.-butoxy, or substituted lower alkoxy, for example benzyloxy, 4-nitrobenzyloxy or diphenylmethoxy.

Silyloxy $Y_1$ or $Y_2$ is, for example, tri-lower alkylsilyloxy, for example trimethylsilyloxy.

Sulphonyloxy $Y_1$ or $Y_2$ is, for example, lower alkanesulphonyloxy, for example methanesulphonyloxy, benzenesulphonyloxy or p-toluenesulphonyloxy.

A compound that yields the group $>N-R_1$ is, for example, an alkali metal amide, for example sodium amide or potassium amide, ammonia ($R_1$=hydrogen), a lower alkylamine, for example methylamine ($R_1$=lower alkyl), a carbonic acid amide, for example urea or 1,3-dimethylurea, or a lower alkanecarboxylic acid amide, for example formamide, N-methylformamide, acetamide or N-methylacetamide.

The reaction with a compound that yields the group $>N-R_1$, for example with ammonia or with methylamine, can be carried out stepwise. For example it is possible to obtain first a compound of the formula III in which one of the leaving groups $Y_1$ and $Y_2$ has been replaced by $-NH-R_1$. Such a compound, for example the monoamide, can be isolated or can be converted into a compound of the formula I in situ by removal of $HY_1$ or $HY_2$.

A compound of the formula III in which, for example, $Y_1$ and $Y_2$ represent hydroxy, can first be converted into its anhydride, for example thermally or by dehydration with a customary dehydrating agent, for example acetic anhydride or acetyl chloride. This anhydride can be isolated or can be converted in situ by reaction with a compound that yields the group $>N-R_1$, for example a compound of the formula $H_2N-R_1$, such as ammonia or methylamine, into a compound in which one of the leaving groups $Y_1$ and $Y_2$ has been replaced by $-NH-R_1$. Such a monoamide can subsequently be cyclised to form a compound of the formula I by removing the elements of water.

During the cyclisation, a total of 2 mol of $HY_1$ or $HY_2$, for example HCl or HBr, are freed and are bound, for example, by using an excess of the agent that yields $>N-R_1$, for example ammonia or methylamine.

The reaction is preferably carried out in an inert polar solvent, for example in benzene, toluene, xylene, chlorobenzene, dichlorobenzene, methylene chloride, ether or methanol or in mixtures thereof. The reaction temperature is between $-20°$ and approximately $+180°$ C., and preferably between $+100°$ and $+180°$ C. If an acid halide of the formula III, for example the acid dichloride, is reacted with ammonia, the reaction is preferably carried out while cooling, for example at below 0°.

Process (c)

The cyclisation can be effected, for example, thermally or photochemically.

The thermal cyclisation of the acryloylacrylamides of the formula IV can be carried out without a solvent, but it is preferable to use solutions in high-boiling inert solvents, for example in toluene, xylene, for example 1,3-xylene, mesitylene, chlorobenzene, dichlorobenzene, for example 1,3-dichlorobenzene, nitrobenzene, decalin, hexachlorobutadiene or the like. The compound of the formula IV to be cyclised is dissolved in the solvent in a concentration of from approximately 1M to approximately $10^{-6}$M, preferably in a concentration of from 1M to $10^{-2}$M, and heated in an open vessel, if desired under a protective gas, for example nitrogen or argon, or in a closed pressure vessel at temperatures of from approximately 100° C. to approximately 250° C., preferably from 130° C. to 180° C., for from approximately 1 to approximately 10 hours, preferably from 2 to 5 hours. If the operation is carried out without a solvent, the acryloylacrylamide of the formula IV is, if desired, evaporated under reduced pressure, sprayed in a low-boiling inert solvent or introduced in powder form into a reactor that has been heated to from approximately 200° C. to approximately 500° C. and, optionally with an inert carrier gas, such as nitrogen or argon, passed through the heated reactor.

Acryloylacrylamides of the formula IV can also be cyclised to form compounds of the formula I photochemically, especially when $R_4$ is other than hydrogen. For this purpose, the compounds of the formula IV, together with a triplet sensitiser, for example an aryl ketone, for example benzophenone or acetophenone, are dissolved in a photochemically inert solvent, for example in methylene chloride, diethyl ether, n-pentane, n-hexane, cyclohexane, benzene, toluene or the like, in a concentration of from approximately 1M to approximately $10^{-6}$M and irradiated with ultraviolet light of a wave length of more than 300 nm, for example with a mercury high-pressure or medium-pressure lamp in Pyrex ® glass or with a different filter that is impervious to wavelengths below 300 nm, at temperatures of from approximately $-30°$ C. to approximately $+50°$ C., preferably from 0° C. to 30° C., for from approximately 1 hour to approximately 10 hours, preferably from 2 to 5 hours. Instead of using a photochemically inert solvent and an aryl ketone as the triplet sensitiser, it is preferable to use a di-lower alkyl ketone, for example acetone, 2-butanone or 3-pentanone, or a cycloalkanone, for example cyclohexanone, as the solvent and sensitiser for the photochemical cyclisation.

In order to suppress undesired polymerisation reactions, it is preferable to add to the solutions of the compounds of the formula IV during the thermal or photochemical cyclisation a substance that eliminates radicals, for example hydroquinone, 2,6-di-tert.-butyl-4-methylphenol or bis-(3-tert.-butyl-4-hydroxy-5-methylphenyl)-sulphide, in a concentration of from approximately 0.01% to approximately 5%.

Process (d)

In a compound of the formula V or VI the leaving group $Y_3$ is, for example, halogen, for example chlorine, bromine or iodine, or sulphonyloxy, for example lower alkanesulphonyloxy, for example methanesulphonyloxy, or arylsulphonyloxy, for example benzenesulphonyloxy or p-toluenesulphonyloxy.

Bases suitable for cyclisation are especially non-nucleophilic bases. Examples of such bases are alkali metal salts, for example lithium, sodium or potassium salts, of sterically hindered secondary amines, for example branched di-lower alkylamines, dicycloalkylamines, branched lower alkylcyclohexylamines, bis-(tri-lower alkylsilyl)-amines or the like, for example lithium diisopropylamide, lithium dicyclohexylamide, sodium or potassium bis-(trimethylsilyl)-amide or lithium 2,2,6,6-tetramethylpiperidide. Other suitable bases are alkali metal hydrides, for example potassium hydride, or branched lower alkyllithium compounds, for example tert.-butyllithium.

As the solvent it is preferable to use an ether, for example tetrahydrofuran or dimethoxyethane, to which hexamethylphosphoric acid triamide is optionally added. The reaction is best carried out under an inert gas atmosphere, for example a nitrogen or argon atmosphere, at temperatures of from approximately $-80°$ C. to approximately $+30°$ C., for example at approximately $-30°$ C.

Subsequent operations

The substituents $R_1$, $R_2$, $R_3$ and $R_4$ in a compound of the formula I can be converted within the scope of their definitions into different substituents $R_1$, $R_2$, $R_3$ and $R_4$. For example, a free amino group can be converted into an acylamino group in which $R_2$ represents acyl and $R_3$ represents hydrogen or lower alkyl. These subsequent operations are carried out in a manner known per se, for example as follows:

Acylation of the amino group at the phenyl ring

If, in a resulting compound of the formula I, $R_2$ represents hydrogen, $R_3$ represents hydrogen or lower alkyl and $R_1$ represents hydrogen or a hydrocarbon radical, the free amino group at the phenyl ring can be substituted in a manner known per se by an acyl group $R_2$. If $R_1$ represents hydrogen, the nitrogen atom in position 3 of the bi-cycle (imido nitrogen atom) may, if desired, be protected by one of the amino-protecting groups mentioned above under process (a) or by a different amino-protecting group, such as lower alkanoyl, for example acetyl, lower alkenoyl, for example methacryloyl, or 1-lower alkoxycarbonyl-1-alkenyl, for example 1-methoxycarbonyl-1-vinyl.

This substitution can be effected, for example, by acylation with a suitable acylating agent that introduces the corresponding acyl radical $R_2$.

The amino group at the phenyl ring is in free form or in reactive (that is to say allowing acylation), protected form, for example protected by silyl radicals.

If the amino group at the phenyl ring in a compound of the formula I is substituted by an acyl radical $R^a$—$SO_2$—, there is used as acylating agent, for example, the corresponding sulphonic acid or a reactive functional derivative thereof, especially an anhydride thereof, for example a mixed anhydride. A mixed anhydride of a sulphonic acid is formed, for example, by condensation with an inorganic acid, for example a hydrohalic acid, for example hydrochloric acid, and is, for example, the corresponding sulphonic acid halide, for example the sulphonic acid chloride or bromide.

If the amino group is substituted by an acyl group $R^b$—CO—, there is used as acylating agent, for example, the corresponding carboxylic acid itself or a reactive functional derivative thereof.

A reactive, that is to say forming the carboxamide function, functional derivative of a carboxylic acid is an anhydride of this carboxylic acid, preferably a mixed anhydride. A mixed anhydride is formed, for example, by condensation with a different acid, for example an inorganic acid, for example a hydrohalic acid, and is, for example, the corresponding carboxylic acid halide, for example the carboxylic acid chloride or bromide. A reactive functional derivative of a carboxylic acid of the formula III is also formed by condensation with a lower alkyl semiester of carbonic acid, for example the ethyl or isobutyl semiester of carbonic acid.

If the amino group at the phenyl ring is substituted by an acyl radical R having the meaning $R^a$—O—CO—, $(R^b)(R^b)N$—CO— or $(R^b)(R^b)N$—$SO_2$—, there is used as acylating agent a reactive derivative of the corresponding carbonic acid semiester or of the corresponding carbamic acid or amidosulphonic acid. Such reactive derivatives are, for example, anhydrides, for example mixed anhydrides, that are formed by condensation with inorganic acids, such as hydrohalic acids, for example hydrochloric acid, or, if a carbamic acid is used, are also internal anhydrides, for example isocyanates.

The acylation reactions are preferably carried out in the presence of a suitable acid-binding agent, for example a suitable organic base. A suitable organic base is, for example, an amine, for example a tertiary amine, for example tri-lower alkylamine, for example trimethylamine or triethylamine, a cyclic tertiary amine, for example N-methylmorpholine, a bicyclic amidine, for example a diazabicycloalkene, for example 1,5-diazabicyclo[4.3.0]non-5-ene or 1,8-diazabicyclo[5.4.0]undec-5-ene (DBU), or is a base of the pyridine type, for example pyridine or 4-dimethylaminopyridine. A suitable acid-binding agent is also an inorganic base, for example an alkali metal hydroxide or alkaline earth metal hydroxide, for example sodium, potassium or calcium hydroxide.

The acylation reactions are preferably carried out in an inert, preferably anhydrous, solvent or mixture of solvents, for example in dimethylformamide, methylene chloride, carbon tetrachloride, chlorobenzene, acetone, tetrahydrofuran, ethyl acetate or acetonitrile, or in mixtures thereof, optionally at reduced or elevated temperature, for example in a temperature range of from approximately $-40°$ to approximately $+100°$ C., preferably from approximately $-10°$ C. to approximately $+50°$ C., and optionally in an inert gas atmosphere, for example a nitrogen atmosphere.

The acylation of the free amino group at the phenyl ring can be carried out both in the end product of the formula I and in the intermediates of the formulae II, III and IV according to the method described above.

Substitution of the amino group at the phenyl ring by sulpho

If, in a resulting compound of the formula I, $R_2$ represents hydrogen, $R_3$ represents hydrogen or lower alkyl and $R_1$ represents hydrogen or a hydrocarbon radical, the free amino group at the phenyl ring can be substituted by sulpho in a manner known per se.

This substitution can be effected, for example, by reacting an aminophenyl compound of the formula I with a sulphur trioxide complex with triethylamine.

In order that, in compounds of the formula I in which $R_1$ is hydrogen, the nitrogen atom in position 3 of the bi-cycle (imido nitrogen atom) is not substituted by sulpho, this nitrogen may, if desired, be protected by one of the amino-protecting groups mentioned above.

Alkylation of the amino group at the phenyl ring

If, in a resulting compound of the formula I, $R_2$ and $R_3$ represent hydrogen, the free amino group at the phenyl ring can be substituted by two equivalents of a suitable alkylation agent introducing a lower alkyl radical, for example an alkyl halide, for example methyl bromide, to form a di-lower alkyl-substituted amino group ($R_2$ and $R_3$=lower alkyl). Depending on the reaction conditions, for example also when less than two equivalents of the alkyating agent are used, mixtures of compounds with a di-lower alkyl-substituted amino group, with a mono-lower alkyl-substituted amino group ($R_2$ or $R_3$=lower alkyl) or with an unsubstituted amino group are formed. These mixtures can be separated in a manner known per se, for example by fractional crystallisation or by chromatographic methods.

The free amino group at the phenyl ring can also be protected by one of the above-mentioned customary amino-protecting groups, for example by tert.-butoxycarbonyl, and, after subsequent metallation with a suitable metallating reagent, the amino group protected in this manner can be alkylated with a reactive alkylating compound corresponding to the lower alkyl radical $R_2$ or $R_3$. After removing the amino-protecting groups there is obtained an amino group that is mono-substituted by lower alkyl ($R_2$=H and $R_3$=lower alkyl or $R_2$=lower alkyl and $R_3$=H).

Examples of suitable metallating reagents are lithium diisopropylamide and butyllithium. A reactive compound corresponding to the radical $R_3$ is, for example, a compound of the formula $R_2$—X or $R_3$—X in which X is a nucleofugal leaving group, for example a halogen atom, for example chlorine, bromine or iodine, or a sulphonyloxy group, for example methanesulphonyloxy or p-toluenesulphonyloxy.

If the imido nitrogen atom in compounds in which $R_1$=hydrogen is not to be alkylated, then it may, if necessary, be protected by one of the customary protecting groups mentioned above.

Further subsequent operations

The separation of resulting mixtures of isomers according to the invention into pure isomers is effected in a manner known per se, for example according to physical or chemical methods, for example by fractional crystallisation. It is also possible, however, to use chromatographic methods, for example solid-liquid chromatography. Readily volatile mixtures of isomers can also be separated by distillation or by chromatography.

Acid addition salts are obtained in customary manner, for example by treatment with an acid or a suitable anion exchange reagent.

The process relates also to those embodiments according to which compounds obtained as intermediates are used as starting materials and the remaining process steps are carried out with these, or the process is interrupted at any stage; in addition, starting materials can be used in the form of derivatives or can be formed during the reaction.

The starting materials used and the reaction conditions chosen are preferably those which result in the compounds described above as being especially preferred.

Starting materials

The starting materials and intermediates used in the process for the manufacture of the compounds of the formula I of the present invention are known or, if novel, can be manufactured in a manner known per se. The present invention relates also to novel intermediates and to processes for their manufacture.

Compounds of the formula II in which $R_1$ and $R_4$ have the meanings mentioned under formula I and in which X represents a group that can be converted into the group $-N(R_2)(R_3)$, for example a nitrogen-containing reducible group, for example the nitro, nitroso, hydroxyamino or azido group, a replaceable group, for example halogen, for example chlorine, bromine or iodine, or a derivatised carboxy group, for example the carbamoyl group or azidocarbonyl group, or a protected amino group are novel and the present invention relates also to these. Preferred starting materials of the formula II are compounds in which X represents a nitro group. Compounds of the formula II or salts thereof can be manufactured in a manner known per se, for example, as follows:

(e) a compound of the formula

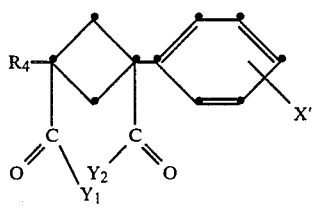

(VII)

in which $R_4$ has the meaning given under formula I and in which $Y_1$ and $Y_2$ represent leaving groups and $X'$ represents one of the above-mentioned groups X or carboxy, or a salt thereof, is cyclised by reaction with a compound that yields the group $-NH-R_1$, or (f) a compound of the formula

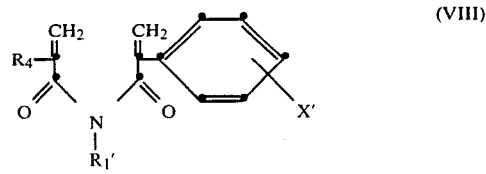

(VIII)

in which $R_1'$ represents a group $R_1$ or an amino-protecting group and $X'$ represents a group X or carboxy, and $R_1$, $R_4$ and X have the meanings given above, or a salt thereof, is cyclised, or (g) a compound of the formula

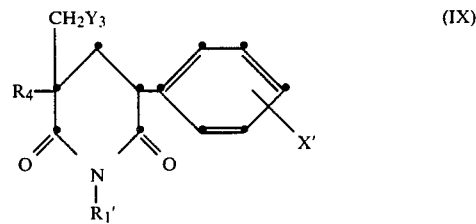

(IX)

or

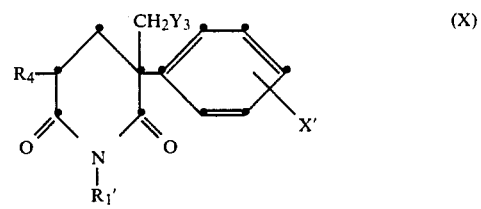

(X)

in which $R_1'$ represents a group $R_1$ or an amino-protecting group, $X'$ represents a group X or carboxy and $Y_3$ represents a leaving group, and $R_1$, $R_4$ and X have the meanings given above, or a salt thereof, is cyclised with a base, and in a resulting compound the carboxy group $X'$ is converted into a replaceable group, for example carbamoyl or azidocarbonyl, and/or the amino-protecting group $R_1'$ is removed and/or, if desired, a compound of the formula II obtainable according to the invention is converted into a different compound of the formula II according to the definition and/or a resulting salt is converted into the free compound or into a different salt and/or a resulting free compound is converted into a salt and/or a resulting mixture of isomers is separated into the individual isomers.

Process (e) can be carried out under reaction conditions analogous to those mentioned above under process (b); process (f) under reaction conditions analogous to those mentioned under process (c), and process (g) under reaction conditions analogous to those mentioned under process (d). The conversion of the carboxy group $X'$ in a compound of the formula II into an azidocarbonyl group or a carbamoyl group can be carried out in accordance with the derivatising processes for aromatic carboxy groups described in Organikum, VEB Deutscher Verlag der Wissenschaften, 15th edition 1976. The removal of amino-protecting groups $R_1'$ is carried out in a manner analogous to that described under process (a).

Suitable amino-protecting groups $R_1'$ and their removal are described above under process (a). Also suitable as amino-protecting groups $R_1'$ are, for example, lower alkanoyl, for example acetyl or propionyl, or lower alkenoyl, for example acryloyl or, especially, methacryloyl. These protecting groups are removed by acidolysis, for example using acetic acid, dichloroacetic acid, trifluoroacetic acid or dilute hydrochloric acid and the like. Also suitable as an amino-protecting group $R_1'$ is, for example, 1-lower alkoxycarbonyl-1-alkenyl, for example 1-methoxycarbonyl-1-vinyl. These protecting groups are removed by oxidation, for example using potassium permanganate, sodium periodate and a catalytic amount of osmium tetroxide, or ozone.

Compounds of the formula III and of the formula VII in which $R_2$, $R_3$ and $R_4$ have the meanings given under formula I, $Y_1$ and $Y_2$ represent leaving groups and $X'$ represents a group that can be converted into the group $-N(R_2)(R_3)$, or carboxy, can be manufactured, for example, as follows: compounds of the formula

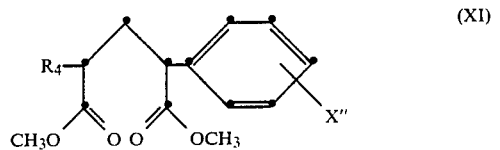

(XI)

in which $R_4$ has the meaning given under formula I and $X''$ represents the group $-N(R_2)(R_3)$, a group that can be converted into the group $-N(R_2)(R_3)$, or carboxy, are alkylated in the α-position in a manner analogous to that described by P. M. Warner et al. in J. Org. Chem. 46, 4795 (1981), using methylene iodide and lithium diisopropylamide, to form an ester function and then cyclised with a base in a manner analogous to that described in process (d) by removing hydrogen iodide, and, finally, the methoxy group of the ester functions is optionally converted into a different leaving group $Y_1$ or $Y_2$.

Methods for converting a methoxy group of an ester into a leaving group, for example into hydroxy, chlorine, bromine, iodine or lower alkoxy, or into an anhydride are described in Houben-Weyl, Vol. VIII, "Sauerstoffverbindungen III", Chapters 4 and 5.

Glutaric acid ester derivatives of the formula XI that are not already known can be obtained by methods analogous to that described in U.S. Pat. No. 2,824,120 from substituted phenylacetic acid esters and optionally α-substituted acrylic esters.

Compounds of the formula IV and of the formula VIII in which $R_1$, $R_2$, $R_3$ and $R_4$ have the meanings given under formula I, $R_1'$ represents a group $R_1$ or an amino-protecting group and $X'$ represents a group that can be converted into the group $-N(R_2)(R_3)$, or carboxy, can be obtained in a manner analogous to that described by A. Alder et al. in Helv. Chim. Acta 65, 2405 (1982) and J. Am. Chem. Soc. 105, 6712 (1983) from α-phenylacrylic acids substituted in the phenyl ring and acrylamides optionally substituted in the α-position and/or at the nitrogen atom.

Compounds of the formulae V and VI or of the formulae IX and X in which $R_1$, $R_2$, $R_3$ and $R_4$ have the meanings given under formula I, $R_1'$ represents a group $R_1$ or an amino-protecting group and $X'$ represents a group that can be converted into a group $-N(R_2)(R_3)$, or carboxy can be obtained, for example, as follows: compounds of the formula

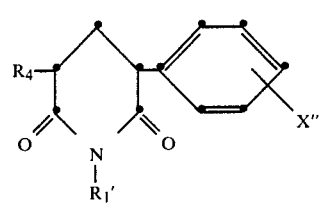

(XII)

in which $R_1'$ and $R_4$ have the above-mentioned meanings and $X''$ represents the group $-N(R_2)(R_3)$, a group that can be converted into the group $-N(R_2)(R_3)$, or carboxy, are iodoalkylated in the α-position of a carbonyl function in a manner analogous to that described by P. M. Warner et al. in J. Org. Chem. 46, 4795 (1981) using methylene iodide and lithium diisopropylamide, or hydroxyalkylated in a corresponding manner using formaldehyde and a non-nucleophilic base and the hydroxy group is then converted in a manner known per se into halogen or a sulphonyloxy group.

The ratio of the isomers of the formulae V and VI or IX and X formed during this reaction is influenced by the nature of the substituents $R_4$ and $X''$, but is not of importance as, during the subsequent cyclisation according to process (d) or (g), uniform compounds of the formulae I and II, respectively, are formed.

Glutarimide derivatives of the formula XII that are not already known can be obtained from the corresponding glutaric acid ester derivative of the formula XI analogously to process (b) by reaction with a compound that introduces the radical $>N-R_1'$, or can be manufactured by hydrogenating correspondingly substituted 2-hydroxy-6-oxo-1,6-dihydropyridines of the formula

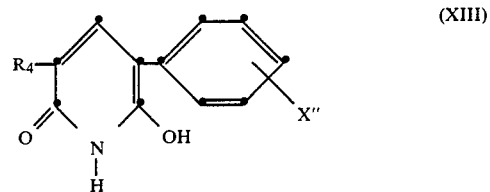

(XIII)

or a tautomeric compound thereof and then optionally alkylating or acylating the imido nitrogen atom using a compound that introduces the radical $R_1'$.

Compounds of the formula XIII are known or can be obtained in the manner described by E. Ziegler et al. in Z. Naturforsch. 33b, 1550 (1978).

The following examples serve to illustrate the invention but do not limit the invention in any way. Temperatures are given in degrees Centigrade.

Abbreviations

IR = infra-red

The $R_f$ values are determined on silica gel thin layer plates. $R_f(CH_2Cl_2)$ means, for example, that the $R_f$ value is determined in the eluant $CH_2Cl_2$ (methylene chloride).

EXAMPLE 1

(a)

1-(4-aminophenyl)-3-n-propyl-3-azabicyclo[3.1.1]heptane-2,4-dione 0.35 g of 5% palladium-on-carbon catalyst is added to a solution of 3.5 g of 1-(4-nitrophenyl)-3-n-propyl-3- azabicyclo[3.1.1]heptane-2,4-dione in 70 ml of ethyl acetate and the whole is hydrogenated under normal pressure and at 30°–35° in a hydrogen atmosphere. When the absorption of hydrogen is complete, the reaction mixture is diluted with 30 ml of methylene chloride and freed of catalyst by filtration over HYFLO Super-Cel ®. The solvent is evaporated off in vacuo, and the residue is recrystallised from a mixture of ethyl acetate/n-hexane, yielding the title compound in the form of white crystals having a melting point of 166°–167°.

IR spectrum in $CHCl_3$: 1685 and 1740 $cm^{-1}$.

Manufacture of the starting material:

(b)

1-(4-nitrophenyl)-3-n-propyl-3-azabicyclo[3.1.1]-eptane-2,4-dione

A solution of 46.1 g of 4-aza-2-(4-nitrophenyl)-4-n-propyl-1,6-heptadiene-3,5-dione and 0.5 g of 2,6-di-tert.-butyl-p-cresol in 900 ml of 1,3-dichlorobenzene is stirred at 170° for 1½ hours. After concentration by evaporation the residue is recrystallised from a methylene chloride/diisopropyl ether mixture, yielding the title compound in the form of pale yellow crystals having a melting point of 141°–143°. The mother liquor is concentrated by evaporation and filtered over silica gel 60 with methylene chloride. After recrystallisation from a methylene chloride/diisopropyl ether mixture, the resulting product yields white crystals having a melting point of 149°–151°.

IR spectrum in $CHCl_3$: 1350, 1685 and 1745 $cm^{-1}$.

(c)

4-aza-2-(4-nitrophenyl)-4-n-propyl-1,6-heptadiene-3,5-dione

A solution of 76.2 g of oxalyl chloride in 500 ml of methylene chloride is added dropwise over a period of 2 hours at room temperature to a stirred suspension of 115.8 g of α-(4-nitrophenyl)-acrylic acid in 5 ml of dimethylformamide and 2.5 liters of methylene chloride. When the addition is complete, the mixture is stirred for a further 2 hours until the evolution of gas has ceased. The resulting solution of 2-(4-nitrophenyl)-acrylic acid chloride is cooled to 0° and added dropwise to a solution, cooled to 0°–5°, of 67.8 g of N-n-propyl-acrylamide and 121 g of triethylamine in 450 ml of methylene chloride. When the addition is complete, the mixture is stirred for 1½ hours at room temperature. After concentration by evaporation, the residue is stirred with 2 liters of ether and filtered with suction, and the residue is again stirred with methylene chloride and again filtered with suction. The ether filtrate is concentrated to dryness by evaporation in vacuo, and the residue is heated with 3 liters of hexane; activated carbon is added and the whole is filtered while hot. After cooling, the title compound is obtained in the form of pale pink crystals having a melting point of 68°–69.5°.

The methylene chloride filtrate is concentrated by evaporation to a volume of approximately 300 ml, filtered with suction and filtered over 1.5 kg of silica gel 60 in ether. After the filtrate has been concentrated by evaporation and recrystallised from hexane there is obtained the title compound, likewise in crystalline form, having a melting point of 69°–70°. Repeat recrystallisation of the combined products from hexane yields a white crystalline product having a melting point of 71.5°–72.5°.

EXAMPLE 2

(a)

1-(4-aminophenyl)-3-methyl-3-azabicyclo[3.1.1]heptane-2,4-dione

In a manner analogous to that described in Example 1a, 6.0 g of 3-methyl-1-(4-nitrophenyl)-3-azabicyclo[3.1.1]-heptane-2,4-dione are dissolved in 120 ml of 2-methoxyethanol, hydrogenated in the presence of 0.6 g of 5% palladium-on-carbon and worked up. Melting point 197°–198° (from ethyl acetate).

IR spectrum in $CHCl_3$: 1680 and 1740 $cm^{-1}$.

Manufacture of the starting material:

(b)

3-methyl-1-(4-nitrophenyl)-3-azabicyclo[3.1.1]-heptane-2,4-dione

In a manner analogous to that described in Example 1b, 37.1 g of 4-aza-4-methyl-2-(4-nitrophenyl)-1,6-heptadiene-3,5-dione and 0.4 g of 2,6-di-tert.-butyl-p-cresol in 370 ml of 1,3-dichlorobenzene are stirred at 170° and worked up. Melting point 185°–188° (from methylene chloride/diisopropyl ether).

IR spectrum in $CHCl_3$: 1350, 1685 and 1740 $cm^{-1}$.

(c)

4-aza-4-methyl-2-(4-nitrophenyl)-1,6-)heptadiene-3,5-dione

The title compound is prepared analogously to Example 1c starting from 115.8 g of α-(4-nitrophenyl)-acrylic acid, 76.2 g of oxalyl chloride and 51.1 g of N-methylacrylamide. The yellow oil is processed further in crude form.

EXAMPLE 3

(a)

1-(4-aminophenyl)-3-isopropyl-3-azabicyclo[3.1.1]-heptane-2,4-dione

In a manner analogous to that described in Example 1a, 2.3 g of 3-isopropyl-1-(4-nitrophenyl)-3-azabicyclo[3.1.1]-heptane-2,4-dione are dissolved in 50 ml of ethyl acetate, hydrogenated in the presence of 0.25 g of 5% palladium-on-carbon and worked up. Melting point 191°–201° (from ethyl acetate/hexane).

IR spectrum in $CHCl_3$: 1680 and 1740 $cm^{-1}$.

Manufacture of the starting material:

(b)

3-isopropyl-1-(4-nitrophenyl)-3-azabicyclo[3.1.1]-heptane-2,4-dione

In a manner analogous to that described in Example 1b, 10.2 g of 4-aza-4-isopropyl-2-(4-nitrophenyl)-1,6-heptadiene-3,5-dione and 0.2 g of 2,6-di-tert.-butyl-p-cresol in 100 ml of 1,3-dichlorobenzene are stirred at 170° and worked up. $R_f(CH_2Cl_2)=0.26$.

IR spectrum in $CHCl_3$: 1350, 1680 and 1740 $cm^{-1}$.

(c)

4-aza-4-isopropyl-2-(4-nitrophenyl)-1,6-heptadiene-3,5-dione

The title compound is prepared analogously to Example 1c starting from 44.6 g of α-(4-nitrophenyl)-acrylic acid, 29.8 g of oxalyl chloride and 21.8 g of N-isopropylacrylamide; oily solid. $R_f(CH_2Cl_2)=0.3$.

EXAMPLE 4

(a)
1-(4-aminophenyl)-3-neopentyl-3-azabicyclo[3.1.1]-heptane-2,4-dione

In a manner analogous to that described in Example 1a, 4.1 g of 3-neopentyl-1-(4-nitrophenyl)-3-azabicyclo[3.1.1]-heptane-2,4-dione are dissolved in 80 ml of ethyl acetate, hydrogenated in the presence of 0.4 g of 5% palladium-on-carbon and worked up. Melting point 141.5°–143° (from diethyl ether).

IR spectrum in $CHCl_3$: 1685 and 1740 $cm^{-1}$.

Manufacture of the starting material:

(b)
3-neopentyl-1-(4-nitrophenyl)-3-azabicyclo[3.1.1]-heptane-2,4-dione

In a manner analogous to that described in Example 1b, 12.1 g of 4-aza-4-neopentyl-2-(4-nitrophenyl)-1,6-heptadiene-3,5-dione and 0.2 g of 2,6-di-tert.-butyl-p-cresol in 120 ml of 1,3-dichlorobenzene are stirred at 170° and worked up. After filtration over silica gel 60 with methylene chloride, the title compound is obtained in the form of yellow crystals having a melting point of 175°–182°. $R_f$(ether)=0.56.

IR spectrum in $CHCl_3$: 1350, 1690 and 1745 $cm^{-1}$.

(c)
4-aza-4-neopentyl-2-(4-nitrophenyl)-1,6-heptadiene-3,5-dione

The title compound is prepared analogously to Example 1c starting from 45.9 g of α-(4-nitrophenyl)-acrylic acid, 30.2 g of oxalyl chloride and 28.0 g of N-neopentylacrylamide. Yellow oil. $R_f$($CH_2Cl_2$)=0.36.

Alternative method of manufacturing the starting material:

(d)
3-neopentyl-1-(4-nitrophenyl)-3-azabicyclo[3.1.1]heptane-2,4-dione 2.4 ml of neopentylamine are added dropwise at room temperature to a suspension of 2.5 g of 1-(4-nitrophenyl)-1,3-cyclobutanedicarboxylic acid anhydride in 6 ml of acetic acid. The mixture is stirred at 120° for 20 hours. After concentration by evaporation, the residue is chromatographed over silica gel with a 2:1 ether/hexane mixture. A fraction is obtained that is identical with the title compound of Example 4b.

(e) 1-(4-nitrophenyl)-1,3-cyclobutanedicarboxylic acid anhydride

A mixture of 10 g of cis-1-(4-nitrophenyl)-1,3-cyclobutanedicarboxylic acid and 100 ml of acetic anhydride is heated under reflux for 2 hours. The reaction mixture is concentrated to dryness by evaporation, and the residue is suspended in toluene, filtered with suction, washed with ether and dried overnight in vacuo. The title compound is obtained in the form of grey crystals having a melting point of 183°–187°.

IR spectrum (KBr disc): 1355, 1780 and 1825 $cm^{-1}$.

(f) cis-1-(4-nitrophenyl)-1,3-cyclobutanedicarboxylic acid

A suspension of 36.3 g of 1-(4-nitrophenyl) 3-n-propyl-3-azabicyclo[3.1.1]-heptane-2,4-dione, 250 ml of acetic acid and 500 ml of 50% sulphuric acid is stirred at 140° for 20 hours. After cooling, the suspension is poured onto ice and extracted four times with ether. The ether extracts are washed twice with aqueous sodium chloride solution, dried with magnesium sulphate and concentrated by evaporation. Toluene is added to the residue and the whole is again concentrated by evaporation in vacuo. After recrystallisation from ethyl acetate there are obtained white crystals having a melting point of 218°–219°.

EXAMPLE 5

(a)
1-(4-aminophenyl)-3-n-decyl-3-azabicyclo[3.1.1]heptane-2,4-dione

In a manner analogous to that described in Example 1a, 6.0 g of 3-n-decyl-1-(4-nitrophenyl)-3-azabicyclo[3.1.1]-heptane-2,4-dione are dissolved in 120 ml of 2-methoxyethanol, hydrogenated in the presence of 0.6 g of 5% palladium-on-carbon and worked up. Melting point 81.5°–82.5° (from ethyl acetate/hexane).

IR spectrum in $CHCl_3$: 1680 and 1740 $cm^{-1}$.

Manufacture of the starting material:

(b)
3-n-decyl-1-(4-nitrophenyl)-3-azabicyclo[3.1.1]heptane-2,4-dione

In a manner analogous to that described in Example 1b, 36.5 g of 4-aza-4-n-decyl-2-(4-nitrophenyl)-1,6-heptadiene-3,5-dione and 0.4 g of 2,6-di-tert.-butyl-p-cresol in 370 ml of 1,3-dichlorobenzene are stirred at 170° and worked up. After filtration over silica gel 60 with an ether/hexane mixture 1:1, the title compound is obtained in the form of a yellow oil. $R_f$(ether)=0.54.

IR spectrum in $CHCl_3$: 1350, 1685 and 1740 $cm^{-1}$.

(c)
4-aza-4-n-decyl-2-(4-nitrophenyl)-1,6-heptadiene-3,5-dione

The title compound is prepared analogously to Example 1c starting from 37.8 g of α-(4-nitrophenyl)-acrylic acid, 24.9 g of oxalyl chloride and 41.7 g of N-n-decylacrylamide. Yellow oil.

EXAMPLE 6

(a)
1-(4-aminophenyl)-3-cyclohexylmethyl-3-azabicyclo[3.1.1]heptane-2,4-dione

In a manner analogous to that described in Example 1a, 6.0 g of 3-cyclohexylmethyl-1-(4-nitrophenyl)-3-azabicyclo-[3.1.1]heptane-2,4-dione are dissolved in 120 ml of 2-methoxyethanol, hydrogenated in the presence of 0.6 g of 5% palladium-on-carbon and worked up. Melting point 140°–146° (from ether). $R_f$(ether)=0.25.

IR spectrum in $CHCl_3$: 1685 and 1740 $cm^{-1}$.

Manufacture of the starting material:

(b) 3-cyclohexylmethyl-1-(4-nitrophenyl)-3-azabicyclo-[3.1.1]heptane-2,4-dione

In a manner analogous to that described in Example 1b, 22.3 g of 4-aza-4-cyclohexylmethyl-2-(4-nitrophenyl)-1,6-heptadiene-3,5-dione and 0.3 g of 2,6-di-tert.-butyl-p-cresol in 220 ml of 1,3-dichlorobenzene are stirred at 170° and worked up. Melting point 191°–194° (from methylene chloride/diisopropyl ether).

IR spectrum in $CHCl_3$: 1350, 1685 and 1740 $cm^{-1}$.

(c)
4-aza-4-cyclohexylmethyl-2-(4-nitrophenyl)-1,6-heptadiene-3,5-dione

The title compound is prepared analogously to Example 1c starting from 47.9 g of α-(4-nitrophenyl)-acrylic acid, 31.5 g of oxalyl chloride and 34.7 g of N-cyclohexylmethylacrylamide; light yellow crystals having a melting point of 92°–93°.

EXAMPLE 7

(a)
1-(4-aminophenyl)-3-cyclohexyl-3-azabicyclo[3.1.1]-heptane-2,4-dione

In a manner analogous to that described in Example 1a, 6.0 g of 3-cyclohexyl-1-(4-nitrophenyl)-3-azabicyclo[3.1.1]-heptane-2,4-dione are dissolved in 120 ml of 2-methoxyethanol, hydrogenated in the presence of 0.6 g of 5% palladium-on-carbon and worked up. Melting point 139°–14020 (from ether).

IR spectrum in $CHCl_3$: 1680 and 1735 $cm^{-1}$.
Manufacture of the starting material:

(b)
3-cyclohexyl-1-(4-nitrophenyl)-3-azabicyclo[3.1.1]-heptane-2,4-dione

In a manner analogous to that described in Example 1b, 34.6 g of 4-aza-4-cyclohexyl-2-(4-nitrophenyl)-1,6-heptadiene-3,5-dione and 0.4 g of 2,6-di-tert.-butyl-p-cresol in 350 ml of 1,3-dichlorobenzene are stirred at 170° and worked up. Melting point 163°–164° (from methylene chloride/diisopropyl ether).

IR spectrum in $CHCl_3$: 1350, 1690 and 1745 $cm^{-1}$.

(c)
4-aza-4-cyclohexyl-2-(4-nitrophenyl)-1,6-heptadiene-3,5-dione

The title compound is prepared analogously to Example 1c starting from 40.5 g of α-(4-nitrophenyl)-acrylic acid, 26.7 g of oxalyl chloride and 26.8 g of N-cyclohexylacrylamide. Melting point 73°–74° (from hexane).

EXAMPLE 8

(a)
1-(4-aminophenyl)-3-(4-methoxybenzyl)-3-azabicyclo[3.1.1]heptane-2,4-dione

In a manner analogous to that described in Example 1a, 5.0 g of 3-(4-methoxybenzyl)-1-(4-nitrophenyl)-3-azabicyclo[3.1.1]heptane-2,4-dione are dissolved in 100 ml of ethyl acetate, hydrogenated in the presence of 1 g of 5% palladium-on-carbon and worked up. Melting point 147°–147.5° (from ether).

IR spectrum in $CHCl_3$: 1680 and 1735 $cm^{-1}$.
Manufacture of the starting material:

(b)
3-(4-methoxybenzyl)-1-(4-nitrophenyl)-3-azabicyclo[3.1.1]heptane-2,4-dione

In a manner analogous to that described in Example 1b, 78.2 g of 4-aza-4-(4-methoxybenzyl)-2-(4-nitrophenyl)-1,6-heptadiene-3,5-dione and 0.3 g of 2,6-di-tert.-butyl-p-cresol in 700 ml of 1,3-dichlorobenzene are stirred at 170° and worked up. Melting point 146°–147° (from toluene/ether).

IR spectrum in $CHCl_3$: 1350, 1685 and 1745 $cm^{-1}$.

(c)
4-aza-4-(4-methoxybenzyl)-2-(4-nitrophenyl)-1,6-heptadiene-3,5-dione

The title compound is prepared analogously to Example 1c starting from 106.1 g of α-(4-nitrophenyl)-acrylic acid, 76.8 g of oxalyl chloride and 95.5 g of N-(4-methoxybenzyl)acrylamide. Melting point 106.5°–107° (from ether).

EXAMPLE 9

(a)
1-(4-aminophenyl)-3-azabicyclo[3.1.1]heptane-2,4-dione

In a manner analogous to that described in Example 1a, 5.0 g of 1-(4-nitrophenyl)-3-azabicyclo[3.1.1]heptane-2,4-dione in 250 ml of 2-methoxyethanol are hydrogenated at 45° in the presence of 0.5 g of 5% palladium-on-carbon and worked up. The title compound is obtained which, after recrystallisation from 2-methoxyethanol, melts at 265° with decomposition.

IR spectrum (KBr disc): 1700 and 1735 $cm^{-1}$.
Manufacture of the starting material:

(b)
1-(4-nitrophenyl)-3-azabicyclo[3.1.1]heptane-2,4-dione

A solution of 283 g of cerium(IV) ammonium nitrate in 400 ml of water is added dropwise at room temperature to a stirred solution of 50 g of 3-(4-methoxybenzyl)-1-(4-nitrophenyl)-3-azabicyclo[3.1.1]heptane-2,4-dione in 1.3 liters of acetonitrile.

When the addition is complete, the mixture is stirred for a further 4 hours. The resulting emulsion is concentrated to half the volume in vacuo and then diluted with 2 liters of water. The product formed is filtered with suction, washed with water and dried in vacuo. The crude product is then dissolved in 3 liters of hot acetonitrile, and the resulting solution is filtered over HYFLO SuperCel ® and the filtrate is concentrated at 60°–70° under a water-jet vacuum until crystallisation begins. The title compound is obtained in the form of brownish crystals having a melting point of above 250°.

IR spectrum (KBr disc): 1355, 1695 and 1720 $cm^{-1}$.

EXAMPLE 10

(a)
1-(4-aminophenyl)-3-benzyl-3-azabicyclo[3.1.1]heptane-2,4-dione

In a manner analogous to that described in Example 1a, 2.46 g of 3-benzyl-1-(4-nitrophenyl)-3-azabicyclo[3.1.1]heptane-2,4-dione are dissolved in 50 ml of ethyl acetate, hydrogenated in the presence of 0.3 g of 5% palladium-on-carbon and worked up. Melting point 164°–165.5° (from ether/ethyl acetate).

IR spectrum in $CHCl_3$: 1690 and 1745 $cm^{-1}$.
Manufacture of the starting material:

(b)
3-benzyl-1-(4-nitrophenyl)-3-azabicyclo[3.1.1]heptane-2,4-dione 4.92 g of 1-(4-nitrophenyl)-3-azabicyclo[3.1.1]heptane-2,4-dione are dissolved in 70 ml of dimethylformamide and, under a nitrogen atmosphere, 1.2 g of sodium hydride (pract. Fluka) are added. After stirring for 30 minutes at room temperature, the mixture is cooled to 0°, and a solution of 4.5 g of benzyl bromide in 10 ml of dimethylformamide is added dropwise thereto. After the addition is complete, the mixture is stirred at room temperature for 4 hours. The excess sodium hydride is destroyed by the addition of methanol, and concentration by evaporation is effected in vacuo. The residue is taken up in ethyl acetate and washed with water and aqueous sodium chloride solution. After drying over magnesium sulphate, the mixture is filtered and concentrated by evaporation. Melting point 150°–152° (from ether).

IR spectrum in CHCl$_3$: 1355, 1690 and 1745 cm$^{-1}$.

EXAMPLE 11

(a)

1-(4-aminophenyl)-3-cyclohexylmethyl-3-azabicyclo[3.1.1]heptane-2,4-dione 2.4 of cis-1-(4-aminophenyl)-1,3-cyclobutanedicarboxylic acid and 1.3 ml of cyclohexylmethylamine are stirred in 100 ml of xylene at 140° for 24 hours in a water separator. The reaction mixture is concentrated to dryness by evaporation in vacuo and then chromatographed over silica gel with ether. The crystalline fraction is identical with the title compound of Example 6a.

Manufacture of the starting material:

(b) cis-1-(4-aminophenyl)-1,3-cyclobutanedicarboxylic acid 5 g of cis-1-(4-nitrophenyl)-1,3-cyclobutanedicarboxylic acid are dissolved in 170 ml of 2-methoxyethanol and hydrogenated in the presence of 0.5 g of 5% palladium-on-carbon. After filtration through HYFLO Super-Cel®, concentration by evaporation is carried out. Light yellow crystals. Melting point 228°–229° (decomposition).

EXAMPLE 12

(a)

1-(4-aminophenyl)-5-methyl-3-n-propyl-3-azabicyclo[3.1.1]heptane-2,4-dione 1.0 g of 5% palladium-on-carbon catalyst is added to a solution of 10.0 g of 5-methyl-1-(4-nitrophenyl)-3-n-propyl-3-azabicyclo[3.1.1]heptane-2,4-dione in 200 ml of ethyl acetate and the whole is hydrogenated under normal pressure and at 30°–35° in a hydrogen atmosphere. When the absorption of hydrogen is complete, the reaction mixture is diluted with 100 ml of methylene chloride and freed of catalyst by filtration over HYFLO Super-Cel®. The solvent is evaporated off in vacuo, and the residue is recrystallised from an ethyl acetate/n-hexane mixture, yielding the title compound in the form of white crystals having a melting point of 135°–136°.

IR spectrum in CHCl$_3$: 1685 and 1740 cm$^{-1}$.

Manufacture of the starting material:

(b)

5-methyl-1-(4-nitrophenyl)-3-n-propyl-3-azabicyclo[3.1.1]heptane-2,4-dione

While stirring, a solution of 23.0 g of 4-aza-6-methyl-2-(4-nitrophenyl)-4-n-propyl-1,6-heptadiene-3,5-dione and 0.23 g of 2,6-di-tert.-butyl-p-cresol in 2.3 liters of acetone is irradiated for 3 hours using a UV lamp (Philips 125 HPK) which is immersed in the reaction solution in a double-walled, water-cooled Pyrex glass shaft. After concentration by evaporation, the residue is recrystallised from a methylene chloride/diisopropyl ether mixture, yielding the title compound in the form of white crystals having a melting point of 128.5°–129.5°.

IR spectrum in CHCl$_3$: 1350, 1685 and 1745 cm$^{-1}$.

(c)

4-aza-6-methyl-2-(4-nitrophenyl)-4-n-propyl-1,6-heptadiene-3,5-dione

A solution of 15.3 g of oxalyl chloride in 100 ml of methylene chloride is added dropwise over a period of 30 minutes at room temperature to a stirred suspension of 23.2 g of α-(4-nitrophenyl)-acrylic acid in 1 ml of dimethylformamide and 600 ml of methylene chloride. When the addition is complete, stirring is continued for a further 30 minutes until the evolution of gas has ceased. The resulting solution of α-(4-nitrophenyl)-acrylic acid chloride is cooled to 0° and added dropwise to a solution, cooled to 0°–5°, of 15.2 g of N-n-propylmethacrylamide and 24.2 g of triethylamine in methylene chloride (100 ml). When the addition is complete, the mixture is stirred at room temperature for 1.5 hours. After concentration by evaporation in vacuo, the residue is stirred with ether, then filtered and concentrated by evaporation.

The residue is stirred with boiling hexane; activated carbon is added and the mixture is filtered while hot. The filtrate is concentrated by evaporation. and the residue is recrystallised from diisopropyl ether. The pale yellow crystalline title compound has a melting point of 62°–63°.

EXAMPLE 13

(a)

1-(4-aminophenyl)-5-ethyl-3-n-propyl-3-azabicyclo[3.1.1]heptane-2,4-dione

In a manner analogous to that described in Example 12a, 6.3 g of 5-ethyl-1-(4-nitrophenyl)-3-n-propyl-3-azabicyclo[3.1.1]-heptane-2,4-dione are dissolved in 120 ml of ethyl acetate, hydrogenated in the presence of 0.6 g of 5% palladium-on-carbon and worked up. Melting point 124.5°–125° (from ether).

IR spectrum in CHCl$_3$: 1685 and 1740 cm$^{-1}$.

Manufacture of the starting material:

(b)

5-ethyl-1-(4-nitrophenyl)-3-n-propyl-3-azabicyclo[3.1.1]heptane-2,4-dione

In a manner analogous to that described in Example 1b, 29.6 g of 4-aza-6-ethyl-2-(4-nitrophenyl)-4-n-propyl-1,6-heptadiene-3,5-dione and 0.27 g of 2,6-di-tert.-butyl-p-cresol in 560 ml of 1,3-dichlorobenzene are stirred at 170° and worked up. Melting point 121°–122° (from diisopropyl ether).

IR spectrum in CHCl$_3$: 1350, 1685 and 1740 cm$^{-1}$.

(c)

4-aza-6-ethyl-2-(4-nitrophenyl)-4-n-propyl-1,6-heptadiene-3,5-dione

The title compound is prepared analogously to Example 12c starting from 34.7 g of α-(4-nitrophenyl)-acrylic acid, 22.8 g of oxalyl chloride and 26 g of N-n-propyl-α-ethylacrylamide. Yellow oil. R$_f$ (n-hexane/ether 1:1)=0.46.

EXAMPLE 14

(a)

1-(4-aminophenyl)-5-isobutyl-3-n-propyl-3-azabicyclo[3.1.1]heptane-2,4-dione

In a manner analogous to that described in Example 12a, 5.2 g of 5-isobutyl-1-(4-nitrophenyl)-3-n-propyl-3- azabicyclo[3.1.1]heptane-2,4-dione in 100 ml of ethyl acetate are hydrogenated in the presence of 0.5 g of 5% palladium-on-carbon and worked up. Melting point 86.5°–87° (from n-hexane/ether).

IR spectrum in $CHCl_3$: 1690 and 1740 $cm^{-1}$.

Manufacture of the starting material:

5-isobutyl-1-(4-nitrophenyl)-3-n-propyl-3-azabicyclo)[3.1.1]heptane-2,4-dione

In a manner analogous to that described in Example 12b, 20.7 g of 4-aza-6-isobutyl-2-(4-nitrophenyl)-4-n-propyl-1,6-heptadiene-3,5-dione are irradiated in the presence of 0.2 g of 2,6-di-tert.-butyl-p-cresol in 1.5 liters of acetone. The reaction product is concentrated by evaporation and then chromatographed over silica gel with n-hexane/ether 1:1. Melting point 87°–88° (from n-hexane/ether).

IR spectrum in $CHCl_3$: 1355, 1690 and 1740 $cm^{-1}$.

(c) 4-aza-6-isobutyl-2-(4-nitrophenyl)-4-n-propyl-1,6-heptadiene-3,5-dione

The title compound is prepared analogously to Example 12c starting from 16.4 g of α-(4-nitrophenyl)-acrylic acid, 10.7 g of oxalyl chloride and 14.4 g of N-n-propyl-αisobutylacrylamide; yellow oil.

EXAMPLE 15

(a) 1-(4-aminophenyl)-5-phenyl-3-n-propyl-3-azabicyclo[3.1.1]heptane-2,4-dione

In a manner analogous to that described in Example 12a, 1.8 g of 1-(4-nitrophenyl)-5-phenyl-3-n-propyl-3-azabicyclo[3.1.1]heptane-2,4-dione are dissolved in 40 ml of ethyl acetate, hydrogenated in the presence of 0.2 g of 5% palladium-on-carbon and worked up. Melting point 144°–145° (from n-hexane/ether).

IR spectrum in $CHCl_3$: 1685 and 1735 $cm^{-1}$.

Manufacture of the starting material:

(b) 1-(4-nitrophenyl)-5-phenyl-3-n-propyl-3-azabicyclo[3.1.1]heptane-2,4-dione

In a manner analogous to that described in Example 12b, 3.6 g of 4-aza-2-(4-nitrophenyl)-6-phenyl-4-n-propyl-1,6-heptadiene-3,5-dione are irradiated in the presence of 0.04 g of 2,6-di-tert.-butyl-p-cresol in 250 ml of acetone. The reaction product is concentrated by evaporation and then chromatographed over silica gel with toluene/ethyl acetate 15:1. Melting point 144°–146° (from toluene/ether).

IR spectrum in $CHCl_3$: 1350, 1695 and 1745 $cm^{-1}$.

(c) 4-aza-2-(4-nitrophenyl)-6-phenyl-4-n-propyl-1,6-heptadiene-3,5-dione

The title compound is prepared analogously to Example 12c starting from 36.7 g of α-(4-nitrophenyl)-acrylic acid, 24.1 g of oxalyl chloride and 35.8 g of N-n-propyl-α-phenylacrylamide; white crystals having a melting point of 98°–99°.

EXAMPLE 16

(a) 1,5-di-(4-aminophenyl)-3-n-propyl-3-azabicyclo[3.1.1]heptane-2,4-dione

In a manner analogous to that described in Example 12a, 0.4 g of 1,5-di-(4-nitrophenyl)-3-n-propyl-3-azabicyclo[3.1.1]heptane-2,4-dione are dissolved in 15 ml of ethyl acetate, hydrogenated in the presence of 80 mg of 5% palladium-on-carbon and worked up. Melting point 149°–150° (from ether/methylene chloride).

IR spectrum in $CHCl_3$: 1685 and 1735 $cm^{-1}$.

Manufacture of the starting material:

(b) 1,5-di-(4-nitrophenyl)-3-n-propyl-3-azabicyclo[3.1.1]heptane-2,4-dione

In a manner analogous to that described in Example 1b, 6 g of 4-aza-2,6-di-(4-nitrophenyl)-4-n-propyl-1,6-heptadiene-3,5-dione and 0.08 g of 2,6-di-tert.-butyl-p-cresol in 85 ml of 1,3-dichlorobenzene are stirred at 170° and worked up. Column chromatography of the crude product over silica gel with toluene/ethyl acetate 4:1 yields the title compound which, after recrystallisation from a toluene/ether mixture, melts at 237°–238°.

IR spectrum in $CHCl_3$: 1350, 1690 and 1740 $cm^{-1}$.

(c) 4-aza-2,6-di-(4-nitrophenyl)-4-n-propyl-1,6-heptadiene-3,5-dione

The title compound is prepared analogously to Example 12c starting from 19.3 g of α-(4-nitrophenyl)-acrylic acid, 12.7 g of oxalyl chloride and 18 g of N-n-propyl-α-(4-nitrophenyl)-acrylamide. White crystals having a melting point of 177°–178°.

EXAMPLE 17

(a) 1-(4-aminophenyl)-5-methyl-3-azabicyclo[3.1.1]heptane-2,4-dione

In a manner analogous to that described in Example 12a, 3.7 g of 5-methyl-1-(4-nitrophenyl)-3-azabicyclo[3.1.1]heptane-2,4-dione in 80 ml of 2-methoxyethanol are hydrogenated in the presence of 0.4 g of 5% palladium-on-carbon and worked up. Melting point 216° (from ethanol).

IR spectrum in $CHCl_3$: 1715 and 1745 $cm^{-1}$.

Manufacture of the starting material:

(b) 5-methyl-1-(4-nitrophenyl)-3-azabicyclo[3.1.1]heptane-2,4-dione

At 60°, ammonia is introduced into a stirred suspension of 0.9 g 3-methyl-1-(4-nitrophenyl)-1,3-cyclobutanedicarboxylic acid anhydride in 50 ml of 1,3-dichlorobenzene. After the amido acid has formed, the mixture is heated at reflux for 8 hours, and the reaction solution is then filtered with suction while hot. On cooling, the title compound is formed in the form of brownish-yellow crystals. Melting point 242°–244° (from ethyl acetate).

IR spectrum (KBr disc): 1360, 1700 and 1745 $cm^{-1}$.

(c) 3-methyl 1-(4-nitrophenyl)-1,3-cyclobutanedicarboxylic acid anhydride

A mixture of 10 g of cis-3-methyl-1-(4-nitrophenyl)-1,3-cyclobutanedicarboxylic acid and 100 ml of acetic anhydride is heated under reflux for 2 hours. The reaction mixture is concentrated to dryness by evaporation, and the residue is suspended in toluene, filtered with suction, washed with ether and dried in vacuo. The title compound is obtained in the form of grey crystals having a melting point of 201°–202°.

IR spectrum (KBr disc): 1350, 1765 and 1820 cm$^{-1}$.

(d)

cis-3-methyl-1-(4-nitrophenyl)-1,3-cyclobutanedicarboxylic acid

A suspension of 46 g of 5-methyl-1-(4-nitrophenyl)-3-n-propyl-3-azabicyclo[3.1.1]heptane-2,4-dione, 250 ml of acetic acid and 500 ml of 50% sulphuric acid is stirred for 20 hours at 140°. After cooling, the suspension is poured onto ice and extracted three times with ether. The ether extracts are washed with water, dried with magnesium sulphate and concentrated by evaporation. The title compound is obtained by recrystallisation from ethyl acetate. Melting point 231° (decomposition).

EXAMPLE 18

1-(4-acetylaminophenyl)-3-n-propyl-3-azabicyclo[3.1.1]heptane-2,4-dione

A solution of 0.11 ml of acetic anhydride in 0.5 ml of tetrahydrofuran is added dropwise to a solution of 260 mg of 1-(4-aminophenyl)-3-n-propyl-3-azabicyclo[3.1.1heptane-2,4-dione and 6 mg of 4-dimethylaminopyridine in 8 ml of tetrahydrofuran. After stirring at room temperature for 2½ hours, two drops of ethanol are added to the reaction mixture and stirring is continued for a further 15 minutes. After concentration by evaporation and subsequent recrystallisation from ethyl acetate/petroleum ether, the title compound is obtained in the form of white crystals having a melting point of 138.5°–139.5°. R$_f$(methylene chloride/methanol/glacial acetic acid 40:5:1)=0.55.

EXAMPLE 19

1-(4-dimethylaminophenyl)- and 1-(4-methylaminophenyl)-3-n-propyl-3-azabicyclo[3.1.1]heptane-2,4-dione While stirring, a solution of 15 ml of dimethyl sulphate in 60 ml of tetrahydrofuran is added to a solution of 20.3 g of 1-(4-aminophenyl)-3-n-propyl-3-azabicyclo[3.1.1]heptane-2,4-dione in 470 ml of tetrahydrofuran. A solution of 21.9 ml of triethylamine in 40 ml of tetrahydrofuran is then added dropwise, while stirring, over a period of 6 hours. After stirring for a further 10 hours, 2.5 ml of 15% aqueous ammonia solution is added to the reaction mixture. After concentration by evaporation, water is added to the residue, and extraction is carried out with methylene chloride. The organic phase is separated off, dried over magnesium sulphate, filtered and concentrated by evaporation. After chromatography over silica gel with hexane/ethyl acetate 2:1 there is obtained 1-(4-dimethylaminophenyl)-3-n-propyl-3-azabicyclo[3.1.1]heptane-2,4-dione, R$_f$ (hexane/ethyl acetate 1:1)=0.45, melting point 139°–140° C. (from ethanol); and 1-(4-methylaminophenyl)-3-n-propyl-3-azabicyclo[3.1.1]heptane-2,4-dione, R$_f$ (hexane/ethyl acetate 1:1)=0.35, melting point 134°–135° (from ethanol).

EXAMPLE 20

1-(4-N-acetyl-N-methylaminophenyl)-3-n-propyl-3-azabicyclo[3.1.1]heptane-2,4-dione A mixture of 272 mg of 1-(4-N-methylaminophenyl)-3-n-propyl-3-azabicyclo[3.1.1]heptane-2,4-dione, 10 ml of tetrahydrofuran, 6 mg of 4-dimethylaminopyridine and 0.11 ml of acetic anhydride is stirred at room temperature for 2 hours. Two drops of methanol are then added to the reaction mixture, which is then stirred for a further 15 minutes and concentrated by evaporation. The residue is partitioned twice between ethyl acetate and water. The combined organic phases, dried over MgSO$_4$, are filtered and concentrated by evaporation. The oily residue is crystallised from ethyl acetate/petroleum ether. The title compound is obtained in the form of white crystals having a melting point of 144°–146°. R$_f$ (methylene chloride/methanol 10:1)=0.55.

EXAMPLE 21

1-(4-methanesulphonylaminophenyl)-3-n-propyl-3-azabicyclo[3.1.1]heptane-2,4-dione A solution of 0.31 ml of methanesulphonic acid chloride in 3 ml of methylene chloride is added at room temperature to a solution of 1.03 g of 1-(4-aminophenyl)-3-n-propyl-3azabicyclo[3.1.1]heptane-2,4-dione and 24 mg of 4-dimethylaminopyridine in 10 ml of pyridine. After stirring for 5 hours, 50 ml of water are added, and the mixture is left to stand overnight at 0°–5°. Extraction is carried out with methylene chloride, and the organic phase is washed in succession with water, cold 2N hydrochloric acid, water, semi-saturated bicarbonate solution and water. After drying over magnesium sulphate, the mixture is filtered and concentrated by evaporation, and the residue is recrystallised from methanol. The title compound is obtained in the form of white crystals having a melting point of 159°–160°. R$_f$(hexane/ethyl acetate 1:1)=0.15.

EXAMPLE 22

(a)

1-(4-aminophenyl)-3-ethyl-3-azabicyclo[3.1.1]heptane-2,4-dione

In a manner analogous to that described in Example 1a, 2.33 g of 3-ethyl-1-(4-nitrophenyl)-3-azabicyclo[3.1.1]heptane-2,4-dione in 70 ml of methanol are hydrogenated in the presence of 0.15 g of palladium-on-carbon and worked up. Melting point 159°–162° (from ethyl acetate/petroleum ether).

Manufacture of the starting material:

(b)

3-ethyl-1-(4-nitrophenyl)-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 2.33 g of ethyl iodide dissolved in 10 ml of N,N-dimethylformamide are then added dropwise thereto. When the reaction is complete, the reaction mixture is freed of N,N-dimethylformamide. The residue is partitioned between ethyl acetate and water, and the organic phase is dried over magnesium sulphate and, after concentration by evaporation, the product is obtained in the form of a solid. Melting point 175°–179°. R$_f$(ethyl acetate/hexane 4:1)=0.52.

EXAMPLE 23

(a)

1-(4-aminophenyl)-3-n-butyl-3-azabicyclo[3.1.1]heptane-2,4-dione

In a manner analogous to that described in Example 1, 2.08 g of 3-n-butyl-1-(4-nitrophenyl)-3-azabicyclo[3.1.1]heptane-2,4-dione in 60 ml of ethanol are hydrogenated in the presence of 0.15 g of palladium-on-carbon and worked up. Melting point 178°–179° (from ethyl acetate).

Manufacture of the starting material:

(b) 3-n-butyl-1-(4-nitrophenyl)-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 1.6 ml of n-butyl bromide dissolved in 10 ml of N,N-dimethylformamide are then added dropwise thereto. When the reaction is complete, the reaction mixture is freed of N,N-dimethylformamide. The residue is partitioned between ethyl acetate and water, and the organic phase is dried over magnesium sulphate and, after concentration by evaporation and subsequent recrystallisation from ethyl acetate/petroleum ether, the product is obtained having a melting point of 120°–123°.

EXAMPLE 24

(a) 1-(4-aminophenyl)-3-isobutyl-3-azabicyclo[3.1.1]heptane-2,4-dione

In a manner analogous to that described in Example 1, 2.0 g of 3-isobutyl-1-(4-nitrophenyl)-3-azabicyclo[3.1.1]-heptane-2,4-dione in 100 ml of ethanol are hydrogenated in the presence of 0.1 g of palladium-on-carbon and worked up. Melting point 158°–160° (from ethyl acetate/petroleum ether).

Manufacture of the starting material:

(b) 3-isobutyl-1-(4-nitrophenyl)-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 2.76 g of isobutyl iodide dissolved in 10 ml of N,N-dimethylformamide are then added dropwise thereto. When the reaction is complete, the reaction mixture is freed of N,N-dimethylformamide. The residue is partitioned between ethyl acetate and water, and the organic phase is dried over magnesium sulphate and, after concentration by evaporation and purification by chromatography over silica gel in the system ethyl acetate/hexane 1:2, the product is obtained in the form of a solid. Melting point 136°–137°. $R_f$ (ethyl acetate/hexane 4:1)=0.6.

EXAMPLE 25

(a) 1-(4-aminophenyl)-3-n-pentyl-3-azabicyclo[3.1.1]heptane-2,4-dione

In a manner analogous to that described in Example 1, 2.58 g of 1-(4-nitrophenyl)-3-n-pentyl-3-azabicyclo[3.1.1]heptane-2,4-dione in 75 ml of ethanol are hydrogenated in the presence of 0.15 g of palladium-on-carbon and worked up. Melting point 92°–94° (from ethyl acetate/petroleum ether).

Manufacture of the starting material:

(b) 1-(4-nitrophenyl)-3-n-pentyl-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 2.96 g of n-pentyl iodide dissolved in 10 ml of N,N-dimethylformamide are then added dropwise thereto. When the reaction is complete, the reaction mixture is freed of N,N-dimethylformamide. The residue is partitioned between ethyl acetate and water, and the organic phase is dried over magnesium sulphate and, after concentration by evaporation, the product is obtained having a melting point of 75°–79°.

EXAMPLE 26

(a) 1-(4-aminophenyl)-3-n-heptyl-3-azabicyclo[3.1.1]heptane-2,4-dione

In a manner analogous to that described in Example 1, 2.1 g of 3-n-heptyl-1-(4-nitrophenyl)-3-azabicyclo[3.1.1]heptane-2,4-dione in 100 ml of ethanol are hydrogenated in the presence of 0.1 g of palladium-on-carbon and worked up. After purification by column chromatography on silica gel with the system hexane/ethyl acetate 1:1, the title compound is obtained in the form of wax-like crystals. Melting point 69°–71°. $R_f$ (hexane/ethyl acetate 1:1)=0.25.

Manufacture of the starting material:

(b) 3-n-heptyl-1-(4-nitrophenyl)-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 2.68 g of n-heptyl bromide dissolved in 10 ml of N,N-dimethylformamide are then added dropwise thereto. When the reaction is complete, the reaction mixture is freed of N,N-dimethylformamide. The residue is partitioned between ethyl acetate and water, and the organic phase is dried over magnesium sulphate. After concentration by evaporation and purification by chromatography over silica gel in the system ethyl acetate/hexane 2:5, the product is obtained in the form of a solid. Melting point 91°–92°. $R_f$(ethyl acetate/hexane 4:1)=0.63.

EXAMPLE 27

(a) 3-allyl-1-(4-aminophenyl)-3-azabicyclo[3.1.1]heptane-2,4-dione

A mixture of 1.97 g of 3-allyl-1-(4-nitrophenyl)-3-azabicyclo[3.1.1]heptane-2,4-dione and 5.2 g of tin powder in 14 ml of water and 14 ml of concentrated hydrochloric acid is stirred at 100° for 1.5 hours. After cooling to room temperature, the reaction mixture is diluted with a little water, filtered and rendered alkaline by the addition of sodium hydroxide solution. The reaction mixture is extracted with ethyl acetate, and the organic phase is washed neutral with dilute sodium chloride solution, dried over magnesium sulphate and concentrated by evaporation. Melting point 176°–178° (from ethyl acetate/petroleum ether).

Manufacture of the starting material:

(b)
3-allyl-1-(4-nitrophenyl)-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 1.27 ml of allyl bromide dissolved in 10 ml of N,N-dimethylformamide are then added dropwise thereto. When the reaction is complete, the reaction mixture is freed of N,N-dimethylformamide. The residue is partitioned between ethyl acetate and water, and the organic phase is dried over magnesium sulphate and, after concentration by evaporation and subsequent recrystallisation from ethyl acetate/petroleum ether, the product is obtained having a melting point of 146°–147°.

EXAMPLE 28

(a)
1-(4-aminophenyl]-3-propargyl-3-azabicyclo[3.1.1]heptane-2,4-dione

A mixture of 1.6 g of 1-(4-nitrophenyl)-3-propargyl-3-azabicyclo[3.1.1]heptane-2,4-dione and 4.2 g of tin powder in 12 ml of water and 12 ml of concentrated hydrochloric acid is stirred at 100° for 1 hour. After cooling to room temperature, the reaction mixture is diluted with a little water, filtered and rendered alkaline by the addition of sodium hydroxide solution. The reaction mixture is extracted with ethyl acetate, and the organic phase is washed neutral with dilute sodium chloride solution, dried over magnesium sulphate and concentrated by evaporation. After purification by chromatography over silica gel in the system ethyl acetate/hexane 1:1, the title compound is obtained. $R_f$ (ethyl acetate/hexane 1:1)=0.15.

Manufacture of the starting material:

(b)
1-(4-nitrophenyl)-3-propargyl-3-azabicyclo[3.1.1]heptane-2,4-dione 0.36 g of sodium hydride is added to a solution of 2.46 g of 1-(4-nitrophenyl)-3-azabicyclo[3.1.1]heptane-2,4-dione in 25 ml of N,N-dimethylformamide and the whole is stirred at room temperature for 30 minutes. 0.97 ml of propargyl bromide dissolved in 10 ml of N,N-dimethylformamide is then added dropwise thereto. When the reaction is complete, the reaction mixture is freed of N,N-dimethylformamide. The residue is partitioned between ethyl acetate and water, and the organic phase is dried over magnesium sulphate and, after concentration by evaporation and subsequent recrystallisation from ethyl acetate/petroleum ether, the product is obtained having a melting point of 166°–168°.

EXAMPLE 29

Lacquer-coated tablets

Lacquer-coated tablets containing 300 mg of 1-(4-aminophenyl)-3-n-propyl-3-azabicyclo[3.1.1]heptane-2,4-dione can be manufactured as follows:

| Composition for 10,000 tablets | |
|---|---|
| 1-(4-aminophenyl)-3-n-propyl-3-azabicyclo[3.1.1]heptane-2,4-dione | 3000.0 g |
| corn starch | 680.0 g |
| colloidal silica | 200.0 g |
| magnesium stearate | 20.0 g |
| stearic acid | 50.0 g |
| sodium carboxymethyl starch | 250.0 g |
| water | q.s. |

A mixture of 1-(4-aminophenyl)-3-n-propyl-3-azabicyclo[3.1.1]heptane-2,4-dione, 50 g of corn starch and the colloidal silica is worked into a moist mass with a starch paste comprising 250 g of corn starch and 2.2 kg of demineralised water. This mass is forced through a sieve of 3 mm mesh width and dried at 45° for 30 minutes in a fluidised bed drier. The dry granulate is pressed through a sieve of 1 mm mesh width, mixed with a previously sieved mixture (1 mm sieve) of 330 g of corn starch, the magnesium stearate, the stearic acid and the sodium carboxymethyl starch, and compressed to form slightly domed tablets.

In a coating vessel of 45 cm diameter, the compacts are covered with a solution of 20 g of shellac and 40 g of hydroxypropylmethylcellulose (low viscosity) in 110 g of methanol and 1350 g of methylene chloride by spraying uniformly for 30 minutes; drying is effected by simultaneously blowing in air at 60°.

Instead of the above-mentioned active ingredient it is also possible to use the same amount of a different active ingredient according to the invention.

We claim:
1. Compounds of the formula

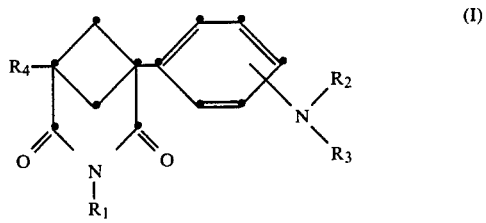

(I)

in which $R_1$ represents hydrogen or a saturated or unsaturated, aliphatic, cycloaliphatic, cycloaliphatic-aliphatic, aromatic or aromatic-aliphatic hydrocarbon radical having up to and including 18 carbon atoms, $R_2$ represents hydrogen, lower alkyl, sulpho or acyl, $R_3$ represents hydrogen or lower alkyl and $R_4$ represents hydrogen, lower alkyl, phenyl or phenyl substituted by —N($R_2$)($R_3$), and pharmaceutically acceptable salts thereof.

2. Compounds according to claim 1 of the formula I in which $R_1$ represents hydrogen, alkyl, alkenyl, lower alkynyl, cycloalkyl, cycloalkenyl, cycloalkyl-lower alkyl, cycloalkyl-lower alkenyl, cycloalkenyl-lower alkyl or unsubstituted or substituted aryl or aryl-lower alkyl, $R_2$ represents hydrogen, lower alkyl, sulpho, lower alkanoyl or lower alkanesulphonyl, $R_3$ represents hydrogen or lower alkyl and $R_4$ represents hydrogen, lower alkyl, phenyl or phenyl substituted by —N($R_2$)($R_3$), and pharmaceutically acceptable salts thereof.

3. Compounds according to claim 1 of the formula I in which $R_1$ represents hydrogen, alkyl having up to and including 12 carbon atoms, lower alkenyl, lower alkynyl, cycloalkyl, cycloalkyl-lower alkyl or unsubstituted or substituted aryl-lower alkyl, $R_2$ represents hydrogen, lower alkyl, lower alkanoyl or lower alkanesulphonyl, $R_3$ represents hydrogen or lower alkyl and $R_4$ represents hydrogen, lower alkyl, phenyl or phenyl substituted by —$N(R_2)(R_3)$, and pharmaceutically acceptable salts thereof.

4. Compounds according to claim 1 of the formula I in which $R_1$ represents hydrogen, lower alkyl, lower alkenyl, lower alkynyl, cycloalkyl or cycloalkyl-lower alkyl, $R_2$ and $R_3$ represent hydrogen and $R_4$ represents hydrogen, lower alkyl, phenyl or phenyl substituted by —$N(R_2)(R_3)$ and pharmaceutically acceptable salts thereof.

5. Compounds according to claim 1 of the formula I in which the group —$N(R_2)(R_3)$ is in the 4-position of the phenyl radical $R_1$ represents hydrogen, lower alkyl, lower alkenyl, lower alkynyl or cycloalkyl-lower alkyl, $R_2$ and $R_3$ represent hydrogen and $R_4$ represents hydrogen or lower alkyl, and pharmaceutically acceptable salts thereof.

6. Compounds according to claim 1 of the formula I in which the group —$N(R_2)(R_3)$ is in the 4-position of the phenyl radical, $R_1$ represents hydrogen, alkyl having up to and including 12 carbon atoms, lower alkenyl, lower alkynyl, cycloalkyl, cycloalkylmethyl or unsubstituted or substituted benzyl and $R_2$, $R_3$ and $R_4$ represent hydrogen, and pharmaceutically acceptable salts thereof.

7. 1-(4-aminophenyl)-3-n-propyl-3-azabicyclo[3.1.1-]heptane-2,4-dione according to claim 1.

8. 1-(4-aminophenyl)-3-methyl-3-azabicyclo[3.1.1-]heptane-2,4-dione according to claim 1.

9. 1-(4-aminophenyl)-3-n-decyl-3-azabicyclo[3.1.1-]heptane-2,4-dione according to claim 1.

10. 1-(4-aminophenyl)-3-cyclohexyl-3-azabicyclo[3.1.1]heptane-2,4-dione according to claim 1.

11. 1-(4-aminophenyl)-3-cyclohexylmethyl-3-azabicyclo[3.1.1]heptane-2,4-dione according to claim 1.

12. A pharmaceutical preparation for treating hormone-dependent dependent tumours and hormonal anomalies containing an effective amount of a compound according to claim 1 together with a significant amount of a pharmaceutical carrier.

13. A method of treating a warm-blooded animal including man suffering from hormone-dependent tumours or hormonal anomalies administering to said animal a therapeutically effective amount of a compound according to claim 1.

14. A method of treating a warm-blooded animal including man suffering from mammary carcinoma administering to said animal a therapeutically effective amount of a compound according to claim 1.

15. A compound of the formula

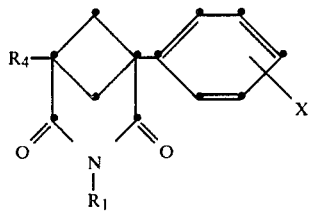

(II)

in which $R_1$ represents hydrogen or a saturated or unsaturated, aliphatic, cycloaliphatic, cycloaliphatic-aliphatic, aromatic or aromatic-aliphatic hydrocarbon radical having up to and including 18 carbon atoms; $R_4$ represents hydrogen lower alkyl, phenyl or phenyl substituted by X; and X represents a nitrogen-containing reducible group, halogen carbamoyl, azidocarbonyl or a protected amino group; or a salt thereof.

16. A compound according to claim 15 in which $R_1$ represents hydrogen, alkyl, alkenyl, lower alkynyl, cycloalkyl, cycloalkenyl, cyclalkyl-lower alkyl, cycloalkyl-lower alkenyl, cycloalkenyl-lower alkyl or unsubstituted or substituted aryl or aryl-lower alkyl wherein "aryl" whether alone or as part of "aryl-lower alkyl" is phenyl or naphthyl and said substituents therefor are selected from lower alkyl, hydroxy, lower alkoxy, acyloxy, amino, lower alkylamino, dilower alkylamino, and halo; $R_4$ represents hydrogen, lower alkyl, phenyl or phenyl substituted by X, and X represents nitro, nitroso, hydroxyamino, azido, halogen, carbamoyl, azidocarbonyl or a protected amino group; or a salt thereof.

17. A compound according to claim 16 in which $R_1$ represents hydrogen, alkyl having up to an including 12 carbon atoms, lower alkenyl, lower alkynyl, cycloalkyl, cycloalkyl-lower alkyl or unsubstituted or substituted aryl-lower alkyl; $R_4$ represents hydrogen, lower alkyl, phenyl or phenyl substituted by X; and X represents nitro, nitroso, hydroxyamino, azido or a protected amino group.

18. A compound according to claim 15 in which $R_1$ represents hydrogen, lower alkyl, lower alkenyl, lower alkynyl, cycloalkyl or cycloalkyl-lower alkyl, $R_4$ represents hydrogen or lower alkyl; and X represents nitro.

19. A compound according to claim 15 in which X is in the 4-position of the phenyl radical, $R_1$ represents hydrogen, lower alkyl, lower alkenyl, lower alkynyl or cycloalkyl-lower alkyl, $R_4$ represents hydrogen or lower alkyl; and X represent nitro.

20. A compound according to claim 16 in which X is in the 4-position of the phenyl radical, $R_1$ represents hydrogen, alkyl having up to and including 12 carbon atoms, lower alkenyl, lower alkynyl, cycloalkyl, cyclalkylmethyl or unsubstituted or substituted benzyl; $R_4$ represent hydrogen; and X represents nitro.

21. 1-(4-nitrophenyl)-3-n-propyl-3-azabicyclo[3.1.1-]heptane-2,4-dione according to claim 15.

22. 1-(4-nitrophenyl)-3-methyl-3-azabicyclo[3.1.1]-heptane-2,4-dione according to claim 15.

23. 1-(4-nitrophenyl)-3-n-decyl-3-azabicyclo[3.1.1-]heptane-2,4-dione according to claim 15.

24. 1-(4-nitrophenyl)-3-cyclohexyl-3-azabicyclo[3.1.1]heptane-2,4-dione according to claim 15.

25. 1-(4-nitrophenyl)-3-cyclohexylmethyl-3-azabicyclo[3.1.1]heptane-2,4-dione according to claim 15.

* * * * *